(12) United States Patent
Li et al.

(10) Patent No.: US 7,928,226 B2
(45) Date of Patent: Apr. 19, 2011

(54) SALTS AND POLYMORPHS OF A VEGF-R INHIBITOR

(75) Inventors: Yi Li, San Francisco, CA (US); Jia Liu, San Diego, CA (US); Anand Sistla, Carlsbad, CA (US); Bruce Joseph Elder, Wynantskill, NY (US); Yufeng Hong, San Diego, CA (US); Paul Kenneth Isbester, Castleton on Hudson, NY (US); Grant Jackson Palmer, Clifton Park, NY (US); Jonathon Stuart Salsbury, Albany, NY (US); Luckner Gerard Ulysse, Albany, NY (US)

(73) Assignee: Agouron Pharmaceuticals Inc., San Diego, CA (US)

( * ) Notice: Subject to any disclaimer, the term of this patent is extended or adjusted under 35 U.S.C. 154(b) by 338 days.

(21) Appl. No.: 12/063,076

(22) PCT Filed: Jul. 27, 2006

(86) PCT No.: PCT/IB2006/002171
§ 371 (c)(1),
(2), (4) Date: Jul. 16, 2008

(87) PCT Pub. No.: WO2007/017740
PCT Pub. Date: Feb. 15, 2007

(65) Prior Publication Data
US 2009/0048254 A1    Feb. 19, 2009

Related U.S. Application Data

(60) Provisional application No. 60/706,332, filed on Aug. 8, 2005, provisional application No. 60/750,189, filed on Dec. 14, 2005.

(51) Int. Cl.
*C07D 413/14* (2006.01)

(52) U.S. Cl. .................................................. 544/128
(58) Field of Classification Search .................. 544/128
See application file for complete search history.

(56) References Cited

U.S. PATENT DOCUMENTS

| 7,381,824 B2 | 6/2008 | Hong et al. |
| 2005/0137395 A1 | 6/2005 | Hong et al. |

FOREIGN PATENT DOCUMENTS

| WO | WO00/18761 | | 4/2000 |
| WO | WO01/74360 | A1 | 10/2001 |
| WO | WO02/12226 | A1 | 2/2002 |
| WO | WO03/074529 | A2 | 9/2003 |
| WO | WO2005/063739 | | 7/2005 |
| WO | WO2007/017740 | A1 | 2/2007 |
| WO | WO2007/006618 | | 10/2007 |

OTHER PUBLICATIONS

Berge et al Journal of Pharmaceutical Sciences, vol. 66(1) (1977) pp. 1-19.*
Berge, S. et al., "Pharmaceutical Salts," *Journal of Pharmaceutical Sciences*, vol. 66, No. 1, Jan. 1977, 1-19.
Corrigan, O., "Salt Forms: Pharmaceutical Aspects," *Encyclopedia of Pharmaceutical Technology*, 2006, 1:1, 3177-3187, Third Edition, Trinity College, University of Dublin, Dublin, Ireland.

* cited by examiner

*Primary Examiner* — Kamal A Saeed
*Assistant Examiner* — Nyeemah Grazier
(74) *Attorney, Agent, or Firm* — Jeffrey H. Tidwell; Matthew J. Pugmire

(57) ABSTRACT

The invention relates to salts and free base forms of N,2-dimethyl-6-[7-(2-morpholinoethoxy)quinolin-4-yloxy]benzofuran-3-carboxamide. The invention further relates to pharmaceutical compositions of these salts and free base forms and methods of treating disorders such as cancer using such compositions.

4 Claims, 35 Drawing Sheets

SALTS AND POLYMORPHS OF A VEGF-R INHIBITOR

This application is the National Stage of International Application No. PCT/IB2006/002171, filed Jul. 27, 2006, which claims the benefit of U.S. Provisional Application No. 60/750,189, filed Dec. 14, 2005 and U.S. Provisional Application No. 60/706,332 filed Aug. 8, 2005, all of which are herein incorporated by reference in their entirety.

BACKGROUND OF THE INVENTION

This invention relates to salt forms and polymorphs of N,2-dimethyl-6-[7-(2-morpholinoethoxy)quinolin-4-yloxy]benzofuran-3-carboxamide that are useful in the treatment of abnormal cell growth, such as cancer, in mammals. This invention also relates to compositions including such salts and polymorphs, and to methods of using such compositions in the treatment of abnormal cell growth in mammals, especially humans.

The compound N,2-dimethyl-6-[7-(2-morpholinoethoxy)quinolin-4-yloxy]benzofuran-3-carboxamide, shown in structural formula 1 in its free base form,

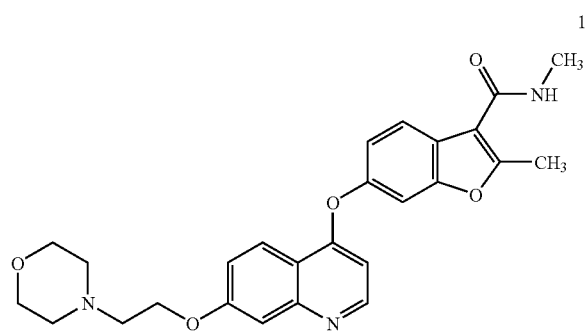

is a potent, selective inhibitor of vascular endothelial growth factor receptor 2 (VEGF-R2). It potently inhibits the tyrosine kinase activity of VEGF-R2 and selectively blocks VEGF-stimulated receptor autophosphorylation, as well as endothelial cell survival. In vivo studies have shown that this compound produced significant inhibition of vascular permeability, tumor angiogenesis, and the growth of human xenograft tumors. This compound has been described in the published U.S. patent application US 2005-0137395, published Jun. 23, 2005, the disclosure of which is incorporated herein by reference in its entirety. Methods of making the free base form of compound 1 are also described in the U.S. provisional application 60/742,847, entitled "METHODS OF PREPARING A VEGF-R INHIBITOR", filed on Dec. 5, 2005.

It is advantageous to have salt and polymorphic forms having improved properties, such as improved crystallinity, dissolution properties, and/or decreased hygroscopicity, while maintaining chemical and enantiomeric stability properties.

SUMMARY OF THE INVENTION

In one embodiment, the present invention provides a bis-maleate salt of N,2-dimethyl-6-[7-(2-morpholinoethoxy)quinolin-4-yloxy]benzofuran-3-carboxamide. In particular aspects of this embodiment, the salt is anhydrous. In a further aspect, the salt is crystalline. In a further aspect the salt is a crystalline anhydrous salt. In a further aspect the salt is a substantially pure polymorph of bis-maleate Form I. In a further aspect, the salt has a powder X-ray diffraction pattern comprising a peak at diffraction angle (2θ) of 18.6±0.1. In a further aspect, the salt has a powder X-ray diffraction pattern comprising peaks at diffraction angles (2θ) of 4.0±0.1, 18.1±0.1, and 18.6±0.1. In a further aspect the salt has a powder X-ray diffraction pattern comprising peaks at diffraction angles (2θ) of 4.0±0.1, 8.1±0.1, 18.1±0.1, 18.6±0.1, 21.6±0.1, and 26.2±0.1. In a further aspect the salt has a powder X-ray diffraction pattern comprising peaks at diffraction angles (2θ) essentially the same as shown in FIG. 1. In a further aspect the salt has a solid state NMR spectrum comprising a $^{13}$C chemical shift at 148.0±0.1 ppm. In a further aspect the salt has a solid state NMR spectrum comprising $^{13}$C chemical shifts at 148.0±0.1, and 162.5±0.1 ppm. In a further aspect the salt has a solid state NMR spectrum comprising $^{13}$C chemical shifts at 148.0±0.1, 118.0±0.1, 124.2±0.1, 143.9±0.1, and 162.5±0.1 ppm. In a further aspect the salt has a solid state NMR spectrum comprising $^{13}$C chemical shifts at positions essentially the same as shown in FIG. 2. In a further aspect the salt has a Raman spectrum comprising Raman shifts at 1589±1, 1402±1, and 755±1 cm$^{-1}$. In a further aspect the salt has a Raman spectrum comprising Raman shifts at positions essentially the same as shown in FIG. 4.

In a further embodiment is a bis-maleate salt of N,2-dimethyl-6-[7-(2-morpholinoethoxy)quinolin-4-yloxy]benzofuran-3-carboxamide, wherein the salt is a solvate. In a particular embodiment the salt is a hydrate. In a further aspect the salt is a crystalline hydrate salt. In a further aspect the salt is a substantially pure polymorph of bis-maleate Form III. In a further aspect the salt has a powder X-ray diffraction pattern comprising a peak at diffraction angle (2θ) of 12.7±0.1. In a further aspect the salt has a powder X-ray diffraction pattern comprising peaks at diffraction angles (2θ) of 6.4±0.1, 12.7±0.1, and 17.3±0.1. In a further aspect the salt has a powder X-ray diffraction pattern comprising peaks at diffraction angles (2θ) of 6.4±0.1, 12.7±0.1, 17.3±0.1, 21.3±0.1, and 25.9±0.1. In a further aspect the salt has a powder X-ray diffraction pattern comprising peaks at diffraction angles (2θ) essentially the same as shown in FIG. 6. In a further aspect the salt has a solid state NMR spectrum comprising a $^{13}$C chemical shift at 132.8±0.1 ppm. In a further aspect the salt has a solid state NMR spectrum comprising $^{13}$C chemical shifts at 99.2±0.1, 125.8±0, and 132.8±0.1 ppm. In a still further aspect the salt has a solid state NMR spectrum comprising $^{13}$C chemical shifts at 99.2±0.1, 125.8±0.1, 132.8±0.1, 142.2±0.1, and 166.1±0.1 ppm. In a still further aspect the salt has a solid state NMR spectrum comprising $^{13}$C chemical shifts at positions essentially the same as shown in FIG. 7. In a further aspect the salt has a Raman spectrum comprising Raman shifts at 761±1, 1405±1, and 1595±1 cm$^{-1}$. In a further aspect the salt has a Raman spectrum comprising Raman shifts at positions essentially the same as shown in FIG. 9.

In a further embodiment, the invention provides a crystalline bis-maleate salt of N,2-dimethyl-6-[7-(2-morpholinoethoxy)quinolin-4-yloxy]benzofuran-3-carboxamide wherein the salt is a mixture of bis-maleate Form I and bis-maleate Form III. Preferably the mixture is a substantially pure mixture of bis-maleate Form I and bis-maleate Form III, where a substantially pure mixture of bis-maleate Forms I and III includes less than 10%, preferably less than 5%, preferably less than 3%, preferably less than 1% by weight of any other physical forms of the bis-maleate salt.

In a further embodiment, the invention provides an amorphous form of the bis-maleate salt of N,2-dimethyl-6-[7-(2-morpholinoethoxy)quinolin-4-yloxy]benzofuran-3-carboxamide. For example, the amorphous form can have a powder X-ray diffraction pattern comprising peaks at diffraction angles (2θ) essentially the same as shown in FIG. 34.

In a further embodiment, the invention provides a crystalline form of free base N,2-dimethyl-6-[7-(2-morpholinoethoxy)quinolin-4-yloxy]benzofuran-3-carboxamide. In a particular embodiment, the free base N,2-dimethyl-6-[7-(2-morpholinoethoxy)quinolin-4-yloxy]benzofuran-3-carboxamide crystalline form is anhydrous. In another embodiment, the free base N,2-dimethyl-6-[7-(2-morpholinoethoxy)quinolin-4-yloxy]benzofuran-3-carboxamide crystalline form is a hydrate.

In a further embodiment, the crystalline form is a polymorph of free base Form 1. In particular, the crystalline form has a powder X-ray diffraction pattern comprising peaks at diffraction angles (2θ) of 19.9±0.1 and 22.0±0.1. Even more particularly, the crystalline form has a powder X-ray diffraction pattern comprising peaks at diffraction angles (2θ) of 13.5±0.1, 19.1±0.1, 19.9±0.1, 22.0±0.1, and 24.1±0.1. Still more particularly, the crystalline form has a powder X-ray diffraction pattern comprising peaks at diffraction angles (2θ) essentially the same as shown in FIG. 11.

In another embodiment, the crystalline form is a polymorph of free base Form 2. In particular, the crystalline form has a powder X-ray diffraction pattern comprising peaks at diffraction angles (2θ) of 10.6±0.1 and 15.3±0.1. Even more particularly the crystalline form has a powder X-ray diffraction pattern comprising peaks at diffraction angles (2θ) of 10.6±0.1, 14.0±0.1, 15.3±0.1, and 16.9±0.1. Still more particularly, the crystalline form has a powder X-ray diffraction pattern comprising peaks at diffraction angles (2θ) essentially the same as shown in FIG. 12.

In another embodiment, the crystalline form is a polymorph of free base Form 3. In particular, the crystalline form has a powder X-ray diffraction pattern comprising peaks at diffraction angles (2θ) of 12.5±0.1 and 21.6±0.1. Even more particularly the crystalline form has a powder X-ray diffraction pattern comprising peaks at diffraction angles (2θ) of 12.5±0.1, 21.2±0.1, 21.6±0.1, and 24.0±0.1. Still more particularly, the crystalline form has a powder X-ray diffraction pattern comprising peaks at diffraction angles (2θ) essentially the same as shown in FIG. 13.

In another embodiment, the crystalline form is a polymorph of free base Form 4. In particular the crystalline form has a powder X-ray diffraction pattern comprising peaks at diffraction angles (2θ) of 6.5±0.1 and 16.0±0.1. Even more particularly the crystalline form has a powder X-ray diffraction pattern comprising peaks at diffraction angles (2θ) of 5.6±0.1, 6.5±0.1, 16.0±0.1, and 19.5±0.1. Still more particularly, the crystalline form has a powder X-ray diffraction pattern comprising peaks at diffraction angles (2θ) essentially the same as shown in FIG. 14.

In another embodiment, the crystalline form is a polymorph of free base Form 5. In particular, the crystalline form has a powder X-ray diffraction pattern comprising peaks at diffraction angles (2θ) of 22.6±0.1 and 23.4±0.1. Even more particularly the crystalline form has a powder X-ray diffraction pattern comprising peaks at diffraction angles (2θ) of 12.1±0.1, 18.4±0.1, 21.0±0.1, 22.6±0.1, and 23.4±0.1. Still more particularly, the crystalline form has a powder X-ray diffraction pattern comprising peaks at diffraction angles (2θ) essentially the same as shown in FIG. 15.

In another embodiment, the crystalline form is a polymorph of free base Form 6. In particular, the crystalline form has a powder X-ray diffraction pattern comprising peaks at diffraction angles (2θ) of 8.4±0.1 and 14.7±0.1. Even more particularly the crystalline form has a powder X-ray diffraction pattern comprising peaks at diffraction angles (2θ) of 8.4±0.1, 14.7±0.1, 17.5±0.1, and 19.6±0.1. Still more particularly, the crystalline form has a powder X-ray diffraction pattern comprising peaks at diffraction angles (2θ) essentially the same as shown in FIG. 16.

In a further embodiment, the present invention relates to a crystalline form of free base N,2-dimethyl-6-[7-(2-morpholinoethoxy)quinolin-4-yloxy]benzofuran-3-carboxamide, wherein the crystalline form has a Raman spectrum comprising Raman shifts essentially the same as shown in any of FIGS. 17 to 22.

In a further embodiment, the present invention relates to an amorphous form of free base N,2-dimethyl-6-[7-(2-morpholinoethoxy)quinolin-4-yloxy]benzofuran-3-carboxamide. For example, the amorphous form can have a powder X-ray diffraction pattern comprising peaks at diffraction angles (2θ) essentially the same as shown in FIG. 35.

The present invention further relates to a bis-hydrobromide salt of N,2-dimethyl-6-[7-(2-morpholinoethoxy)quinolin-4-yloxy]benzofuran-3-carboxamide. In one embodiment the salt the salt is in an anhydrous crystalline form. In a further embodiment the salt is a substantially pure polymorph of bis-HBr Form I. In a further embodiment the crystalline form has a powder X-ray diffraction pattern comprising peaks at diffraction angles (2θ) essentially the same as shown in FIG. 29. In a further embodiment the salt is in a crystalline hydrate form. In a further embodiment the salt is a substantially pure polymorph of bis-HBr Form II. In a further embodiment the crystalline form has a powder X-ray diffraction pattern comprising peaks at diffraction angles (2θ) essentially the same as shown in FIG. 30.

The present invention further provides a pharmaceutical composition comprising the bis-maleate salt, bis-hydrobromide salt, or free base forms of the compound of formula 1 in any of the crystalline or amorphous forms described herein. The present invention further provides a capsule comprising any of the pharmaceutical compositions of the present invention. In particular aspects of this embodiment, the capsule comprises from 0.1 to 50 mg free base equivalent of the bis-maleate salt of N,2-dimethyl-6-[7-(2-morpholinoethoxy) quinolin-4-yloxy]benzofuran-3-carboxamide. In a further aspect the capsule comprises from 0.5 to 25 mg free base equivalent of the bis-maleate salt of N,2-dimethyl-6-[7-(2-morpholinoethoxy)quinolin-4-yloxy]benzofuran-3-carboxamide. In a further embodiment, the capsule comprises from 0.1 to 50 mg of free base N,2-dimethyl-6-[7-(2-morpholinoethoxy)quinolin-4-yloxy]benzofuran-3-carboxamide. In a further aspect the capsule comprises from 0.5 to 25 mg of free base N,2-dimethyl-6-[7-(2-morpholinoethoxy)quinolin-4-yloxy]benzofuran-3-carboxamide. In a further aspect the capsule comprises from 0.1 to 50 mg free base equivalent of the bis-hydrobromide salt of N,2-dimethyl-6-[7-(2-morpholinoethoxy)quinolin-4-yloxy]benzofuran-3-carboxamide. In a further aspect the capsule comprises from 0.5 to 25 mg free base equivalent of the bis-hydrobromide salt of N,2-dimethyl-6-[7-(2-morpholinoethoxy)quinolin-4-yloxy]benzofuran-3-carboxamide.

In another embodiment, the invention provides a method of treating cancer in a mammal, including a human, the method comprising administering to the mammal a therapeutically effective amount of any of the pharmaceutical compositions of the present invention as described herein.

In another embodiment, the invention provides a method of treating cancer in a mammal, the method comprising administering to the mammal, including a human, any of the capsules of the present invention as described herein.

In a particular aspect of any of the preceding method embodiments, the method further comprises administering one or more anti-tumor agents, anti-angiogenesis agents, signal transduction inhibitors, or antiproliferative agents.

The invention also relates to a method for the treatment of abnormal cell growth in a mammal, including a human, comprising administering to said mammal an amount of a compound of formula 1, as defined above, or a pharmaceutically acceptable salt or solvate thereof, that is effective in treating abnormal cell growth. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said method, said abnormal cell growth is a benign proliferative disease, including, but not limited to, psoriasis, benign prostatic hypertrophy or restinosis.

This invention also relates to a method for the treatment of abnormal cell growth in a mammal which comprises administering to said mammal an amount of a compound of formula 1, or a pharmaceutically acceptable salt or solvate thereof, that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

This invention also relates to a pharmaceutical composition for the treatment of abnormal cell growth in a mammal, including a human, comprising an amount of a compound of the formula 1, as defined above, or a pharmaceutically acceptable salt or solvate thereof, that is effective in treating abnormal cell growth, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

The invention also relates to a pharmaceutical composition for the treatment of abnormal cell growth in a mammal, including a human, which comprises an amount of a compound of formula 1, as defined above, or a pharmaceutically acceptable salt or solvate thereof, that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

This invention also relates to a method for the treatment of a disorder associated with angiogenesis in a mammal, including a human, comprising administering to said mammal an amount of a compound of the formula 1, as defined above, or a pharmaceutically acceptable salt or solvate thereof, that is effective in treating said disorder. Such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restenosis; and certain microbial infections including those associated with microbial pathogens selected from adenovirus, hantaviruses, *Borrelia burgdorferi*, *Yersinia* spp., *Bordetella pertussis*, and group A *Streptococcus*.

This invention also relates to a method of (and to a pharmaceutical composition for) treating abnormal cell growth in a mammal which comprises administering an amount of a compound of formula 1, or a pharmaceutically acceptable salt or solvate thereof, and an amount of one or more substances selected from anti-angiogenesis agents, signal transduction inhibitors, and antiproliferative agents, which amounts are together effective in treating said abnormal cell growth in a mammal.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of formula 1 or a pharmaceutically acceptable salt or solvate thereof, in the methods and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No.

99302232.1 (filed Mar. 25, 1999), Great Britain Patent Application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in combination with the compounds of the present invention are AG-3340, RO 32-3555, RS 13-0830, and the compounds recited in the following list:

3-[[4-(4-fluoro-phenoxy)-benzenesulfonyl]-(1-hydroxy-carbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; 3-[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1]octane-3-carboxylic acid hydroxyamide; 3-endo-3-[4-(4-fluoro-phenoxy)-benzenesulfonylamino]-8-oxa-bicyclo[3.2.1]octane-3-carboxylic acid hydroxyamide; and 3-[4-(4-fluoro-phenoxy)-benzenesulfonylamino]-tetrahydro-furan-3-carboxylic acid hydroxyamide; and pharmaceutically acceptable salts, solvates and prodrugs of said compounds.

The compounds of formula 1, and the pharmaceutically acceptable salts and solvates thereof, can also be used in combination with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Massachusettes).

VEGF inhibitors, for example SU-5416 and SU-6668 (Pfizer Inc.), can also be combined with a compound of formula 1 or a pharmaceutically acceptable salt or solvate thereof. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with a compound of formula 1 or a pharmaceutically acceptable salt or solvate thereof. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are herein incorporated by reference in their entirety.

Other antiproliferative agents that may be used with the in the combination methods of the present invention include inhibitors of the enzyme farnesyl protein transferase and inhibitors of the receptor tyrosine kinase PDGFr, including the compounds disclosed and claimed in the following U.S. patent application Ser. Nos. 09/221,946 (filed Dec. 28, 1998); 09/454,058 (filed Dec. 2, 1999); 09/501,163 (filed Feb. 9, 2000); 09/539,930 (filed Mar. 31, 2000); 09/202,796 (filed May 22, 1997); 09/384,339 (filed Aug. 26, 1999); and 09/383,755 (filed Aug. 26, 1999); and the compounds disclosed and claimed in the following U.S. provisional patent applications: 60/168,207 (filed Nov. 30, 1999); 60/170,119 (filed Dec. 10, 1999); 60/177,718 (filed Jan. 21, 2000); 60/168,217 (filed Nov. 30, 1999), and 60/200,834 (filed May 1, 2000). Each of the foregoing patent applications and provisional patent applications is herein incorporated by reference in their entirety.

A compound of formula 1 or a pharmaceutically acceptable salt or solvate thereof may also be used with other agents useful in treating abnormal cell growth or cancer, including, but not limited to, agents capable of enhancing antitumor immune responses, such as CTLA4 (cytotoxic lymphocite antigen 4) antibodies, and other agents capable of blocking CTLA4; and anti-proliferative agents such as other farnesyl protein transferase inhibitors, for example the farnesyl protein transferase inhibitors described in the references cited in the "Background" section, supra. Specific CTLA4 antibodies that can be used in the present invention include those described in U.S. Provisional Application 60/113,647 (filed Dec. 23, 1998) which is herein incorporated by reference in its entirety.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" as defined immediately above.

As used herein, the term "substantially pure" with reference to a particular polymorphic or amorphous form means that the polymorphic amorphous form includes less than 10%, preferably less than 5%, preferably less than 3%, preferably less than 1% by weight of any other physical forms of the compound.

As used herein, the term "essentially the same" with reference to X-ray diffraction peak positions means that typical peak position and intensity variability are taken into account. For example, one skilled in the art will appreciate that the peak positions (2θ) will show some inter-apparatus variability, typically as much as 0.1°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only. Similarly, as used herein, "essentially the same" with reference to solid state NMR spectrum and Raman spectrum is intented to also encompass the variabilities associated with these analytical techniques, which are known to those of skill in the art. For example, $^{13}C$ chemical shifts measured in solid state NMR will typically have a variability of 0.1 ppm, while Raman shifts will typically have a variability of 1 $cm^{-1}$.

DETAILED DESCRIPTION OF THE INVENTION

Several unique physical forms of the compound N,2-dimethyl-6-[7-(2-morpholinoethoxy)quinolin-4-yloxy]benzofuran-3-carboxamide have now been made. The free base compound N,2-dimethyl-6-[7-(2-morpholinoethoxy)quinolin-4-yloxy]benzofuran-3-carboxamide can be prepared according to methods described in U.S. patent application publication no. US 2005-0137395, published Jun. 23, 2005, the entire disclosure of which is incorporated herein by reference. Additional methods of making the free base compound N,2-dimethyl-6-[7-(2-morpholinoethoxy)quinolin-4-yloxy]benzofuran-3-carboxamide are described in the U.S. provisional patent application, entitled "Methods of Preparing a VEGF-R Inhibitor," filed on Dec. 5, 2005 which is also incorporated herein by reference.

Salts of N,2-dimethyl-6-[7-(2-morpholinoethoxy)quinolin-4-yloxy]benzofuran-3-carboxamide are prepared by treating the free base compound with a suitable amount of the chosen mineral or organic acid in an aqueous solvent medium or in a suitable organic solvent, such as methanol, acetonitrile, ethanol, or ethyl acetate. Upon careful evaporation of the solvent, the desired solid salt is obtained. The desired acid salt can also be precipitated from a solution of the free base in an organic solvent by adding to the solution an appropriate mineral or organic acid. Amorphous forms of free base and salts of N,2-dimethyl-6-[7-(2-morpholinoethoxy)quinolin-4-yloxy]benzofuran-3-carboxamide can be prepared by dissolving the free base or salt in an appropriate solvent such as methanol, ethanol, or mixtures thereof, followed by drying to obtain the solid amorphous form.

Crystalline bis-maleate Salt

The bis-maleate salt of N,2-dimethyl-6-[7-(2-morpholinoethoxy)quinolin-4-yloxy]benzofuran-3-carboxamide can be produced with good crystallinity, for example, by dissolving the free base compound in any suitable solvent, such as $CH_2Cl_2$, THF, acetonitrile, ethyl acetate, methanol, or ethanol at an elevated temperature (e.g. ~85° C.), followed by the addition of maleic acid in a suitable solvent. Purification can then be achieved by recrystallization or slurry in appropriate solvents or solvent mixtures, such as mixtures of acetonitrile and ethanol. Other methods of preparing the bis-maleate salt of N,2-dimethyl-6-[7-(2-morpholinoethoxy)quinolin-4-yloxy]benzofuran-3-carboxamide include dissolving the free base compound in any suitable solvent, such as ethyl acetate at an elevated temperature (e.g. ~68° C.), followed by the addition of solid maleic acid. After cooling the solution at a rate of about 20° C. per hour, the resulting bis-maleate salt in crystalline form precipitates and can be collected by filtration.

Figure 1:
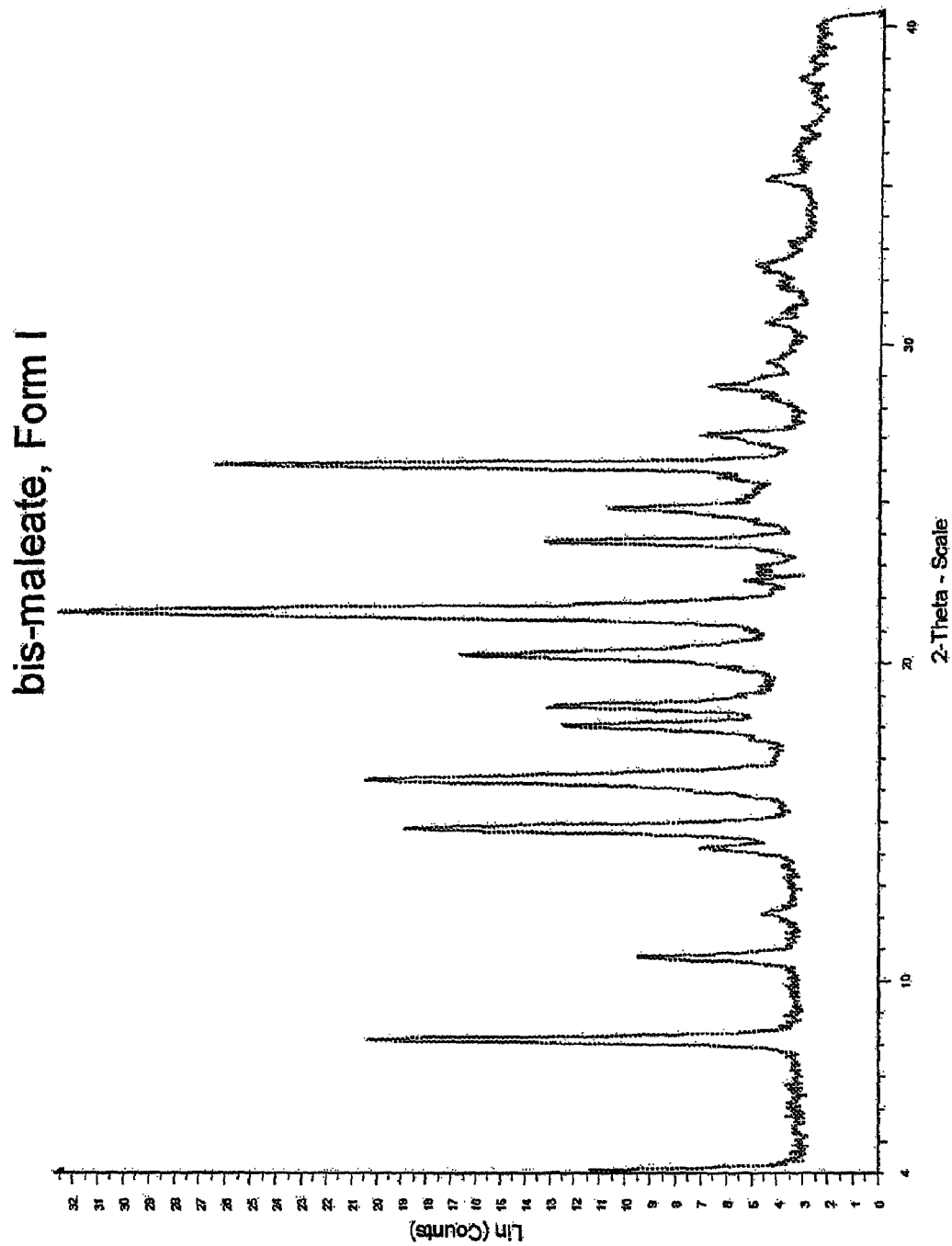
FIG. 1 shows a powder X-ray diffraction pattern of the bis-maleate salt of N,2-dimethyl-6-[7-(2-morpholinoethoxy)quinolin-4-yloxy]benzofuran-3-carboxamide, polymorph Form I.

Two polymorphic forms of the bis-maleate salt of N,2-dimethyl-6-[7-(2-morpholinoethoxy)quinolin-4-yloxy]benzofuran-3-carboxamide have been identified and characterized as indicated in FIGS. 1 to 10, and are designated as bis-maleate Form I and bis-maleate Form III.

bis-maleate Form I can be produced as described previously when making the bis-maleate salt. Bis-maleate Form III can also be converted to bis-maleate Form I by suspending bis-maleate Form III in a suitable solvent such as acetonitrile, followed by seeding with bis-maleate Form I, and stirring at an elevated temperature (e.g. 50° C.) to obtain bis-maleate Form I. The powder X-ray diffraction (PXRD) pattern of bis-maleate Form I is shown in FIG. 1, with corresponding tabulated data shown in Table 1.

TABLE 1

PXRD data tabulation for Form I of the bis-maleate salt of N,2-dimethyl-6-[7-(2-morpholinoethoxy)quinolin-4-yloxy]benzofuran-3-carboxamide.

| 2θ (°) | D value | Intensity (counts) |
|---|---|---|
| 4.0 | 21.9 | 12.1 |
| 8.2 | 10.8 | 21.0 |
| 10.7 | 8.2 | 9.8 |
| 14.2 | 6.2 | 7.6 |
| 14.8 | 6.0 | 19.5 |
| 16.3 | 5.4 | 20.9 |
| 18.1 | 4.9 | 12.9 |
| 18.7 | 4.8 | 13.5 |
| 20.2 | 4.4 | 17.0 |
| 21.5 | 4.1 | 33.2 |
| 23.8 | 3.7 | 13.7 |
| 24.8 | 3.6 | 11.1 |
| 26.2 | 3.4 | 26.9 |
| 27.2 | 3.3 | 7.6 |
| 28.7 | 3.1 | 7.1 |

Figure 2:
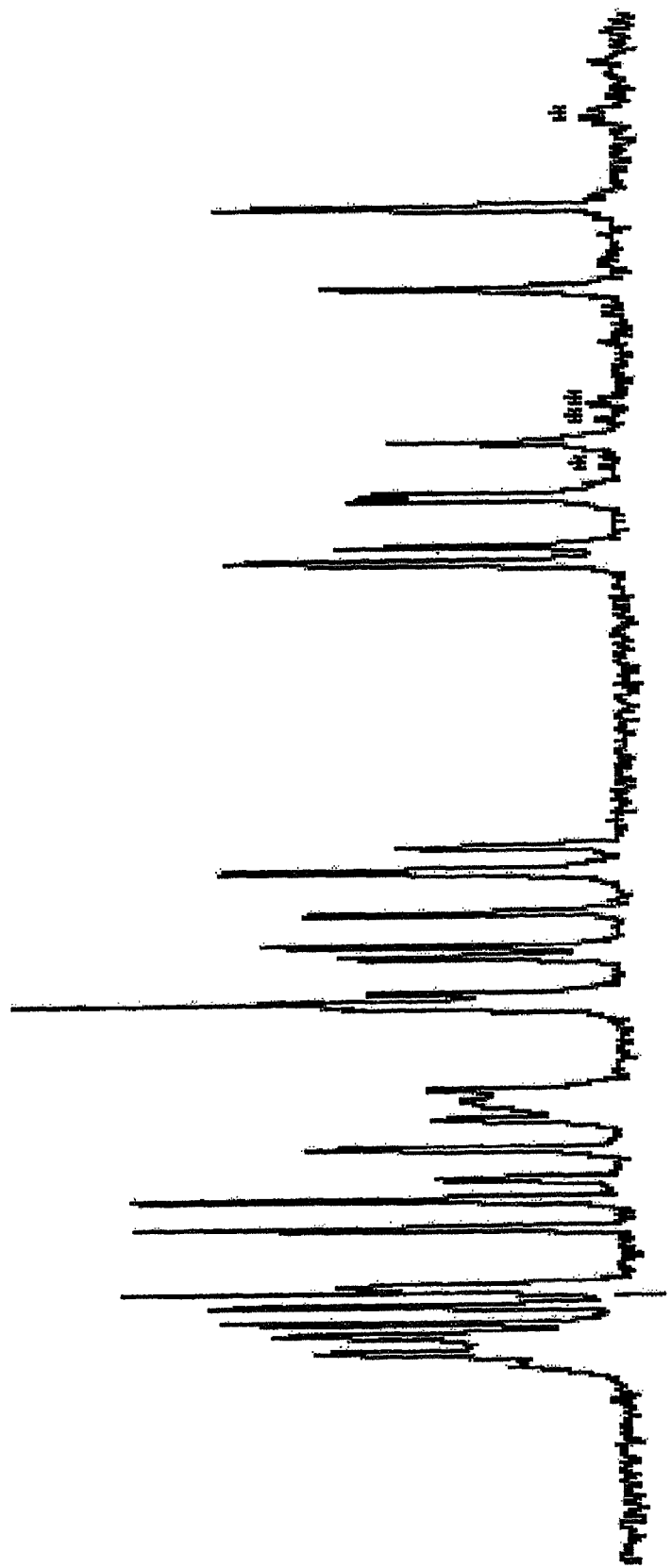
FIG. 2 shows a solid state NMR spectrum of the bis-maleate salt of N,2-dimethyl-6-[7-(2-morpholinoethoxy)quinolin-4-yloxy]benzofuran-3-carboxamide, polymorph Form I.

The solid state NMR spectrum of bis-maleate Form I is shown in FIG. 2, with corresponding tabulated carbon chemical shift data shown in Table 2.

TABLE 2

Carbon chemical shifts of polymorph Form I of the bis-maleate salt of N,2-dimethyl-6-[7-(2-morpholinoethoxy)quinolin-4-yloxy]benzofuran-3-carboxamide.

| Peak Number[a] | $^{13}$C Chemical Shifts[b] [ppm] | Intensity[c] [Arbitrary Units] |
|---|---|---|
| 1 | 173.4 | 2.1 |
| 2 | 171.5 | 6.1 |
| 3 | 169.0 | 6.9 |
| 4 | 167.3 | 7.9 |
| 5 | 165.0 | 8.3 |
| 6 | 163.1 | 9.9 |
| 7 | 162.5 | 5.6 |
| 8 | 154.6 | 9.7 |
| 9 | 150.7 | 9.8 |

TABLE 2-continued

Carbon chemical shifts of polymorph Form I of the bis-maleate salt of N,2-dimethyl-6-[7-(2-morpholinoethoxy)quinolin-4-yloxy]benzofuran-3-carboxamide.

| Peak Number[a] | [13]C Chemical Shifts[b] [ppm] | Intensity[c] [Arbitrary Units] |
|---|---|---|
| 10 | 148.0 | 3.6 |
| 11 | 143.9 | 6.3 |
| 12 | 140.0 | 3.7 |
| 13 | 137.5 | 3.1 |
| 14 | 136.0 | 3.8 |
| 15 | 124.7 | 5.5 |
| 16 | 124.2 | 12.0 |
| 17 | 122.9 | 5.0 |
| 18 | 118.0 | 5.5 |
| 19 | 116.5 | 7.1 |
| 20 | 112.1 | 6.3 |
| 21 | 106.3 | 7.9 |
| 22 | 102.9 | 4.4 |
| 23 | 64.6 | 7.8 |
| 24 | 62.6 | 5.6 |
| 25 | 56.1 | 5.3 |
| 26 | 55.5 | 5.1 |
| 27 | 48.6 | 4.5 |
| 28 | 27.8 | 5.9 |
| 29 | 16.9 | 8.0 |

[a]Peak numbers list all peaks by descending chemical shifts.
[b]Referenced to external sample of solid phase adamantane at 29.5 ppm.
[c]Defined as peak heights. Intensities can vary depending on the actual setup of the CPMAS experimental parameters. CPMAS intensities are not necessarily quantitative.

Figure 3:
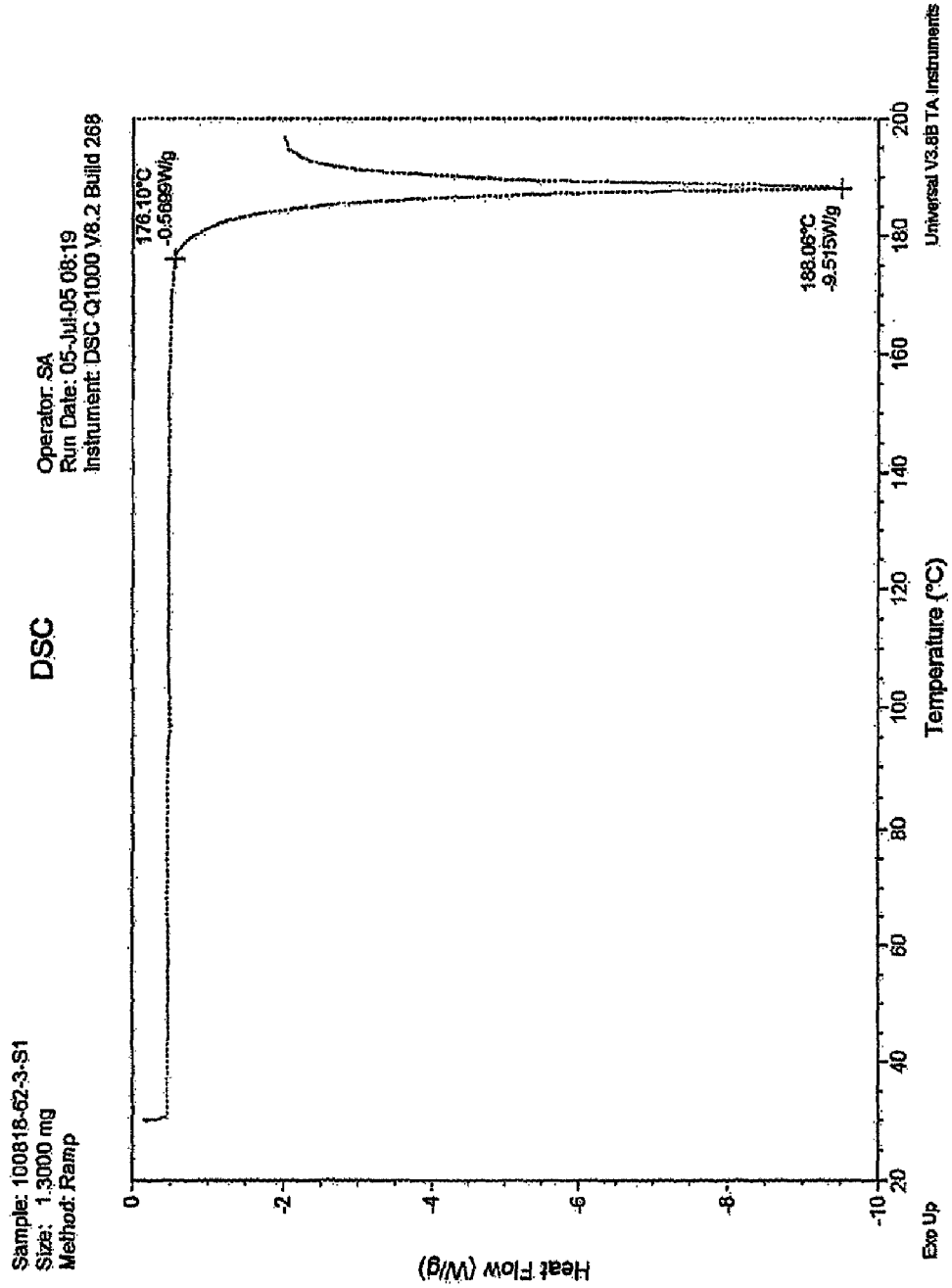
FIG. 3 shows a differential scanning calorimetery (DSC) thermogram of the bis-maleate salt of N,2-dimethyl-6-[7-(2-morpholinoethoxy)quinolin-4-yloxy]benzofuran-3-carboxamide, polymorph Form I.
Figure 4:
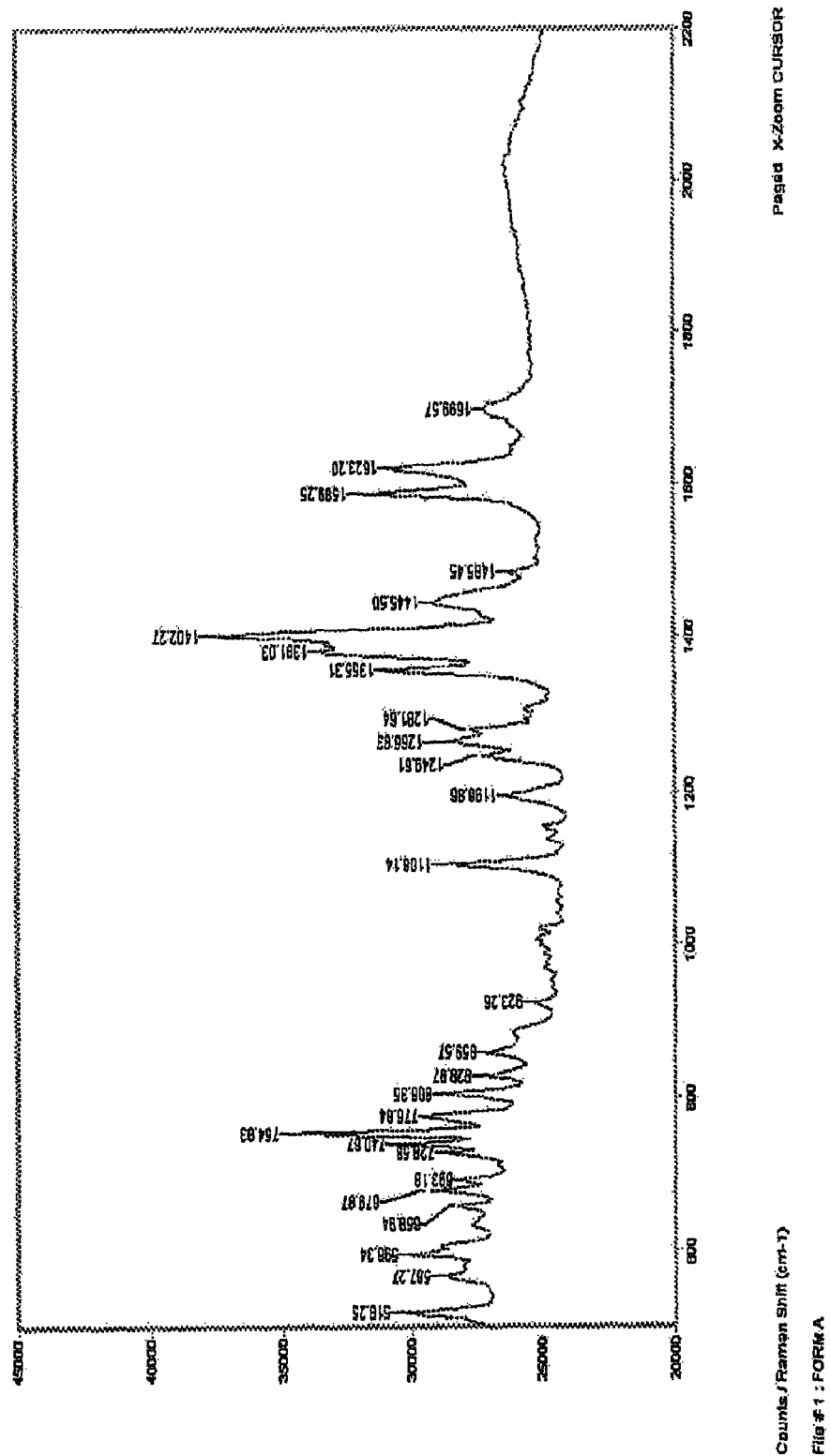
FIG. 4 shows a Raman spectrograph of the bis-maleate salt of N,2-dimethyl-6-[7-(2-morpholinoethoxy)quinolin-4-yloxy]benzofuran-3-carboxamide, polymorph Form I.
Figure 5:
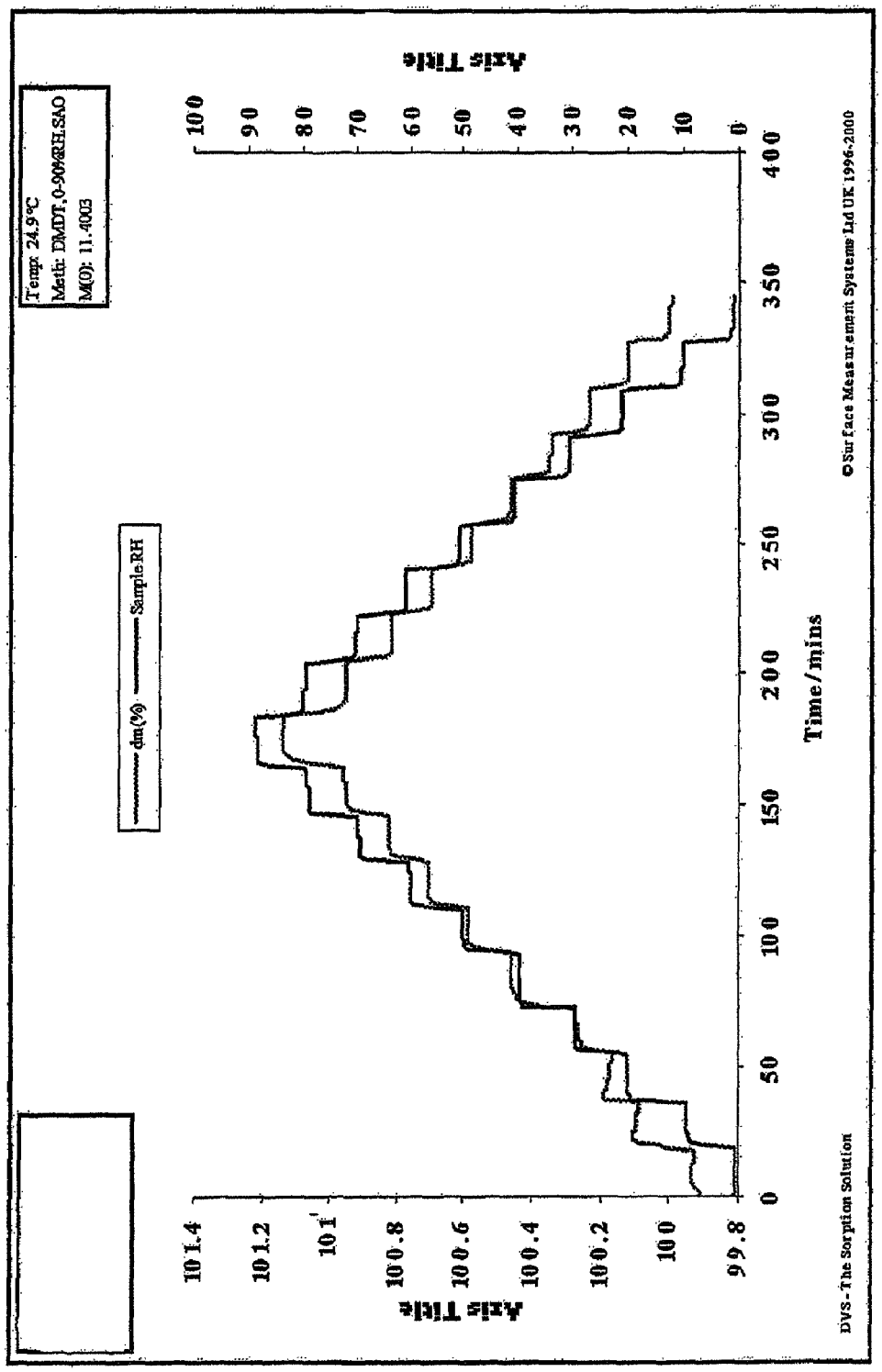
FIG. 5 shows a dynamic vapor sorption profile of the bis-maleate salt of N,2-dimethyl-6-[7-(2-morpholinoethoxy)quinolin-4-yloxy]benzofuran-3-carboxamide, polymorph Form I.

The DSC thermogram for bis-maleate Form I is shown in FIG. 3, the Raman spectrograph for bis-maleate Form I is shown in FIG. 4, and the dynamic vapor sorption profile for bis-maleate Form I is shown in FIG. 5.

Figure 6:
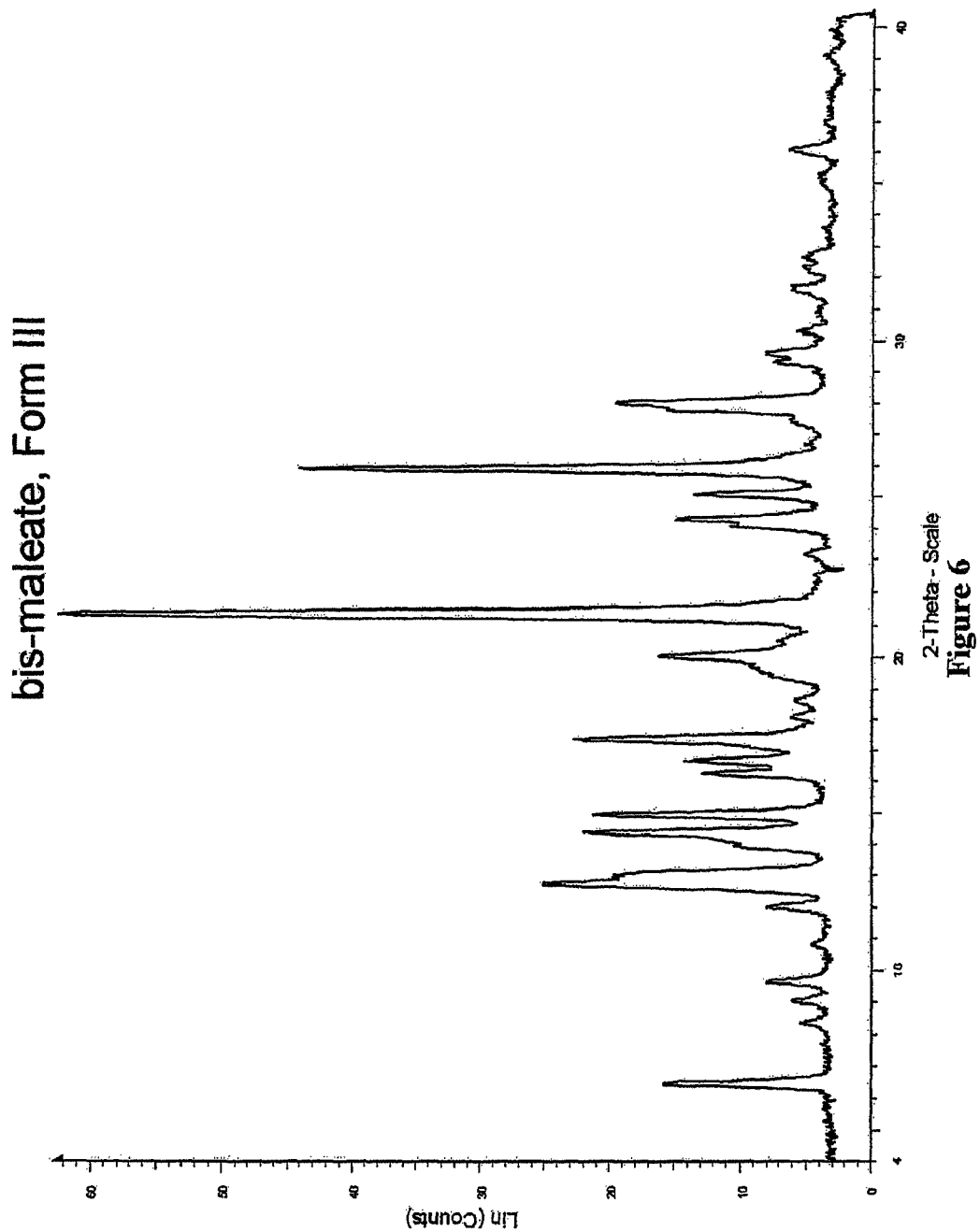
FIG. 6 shows a powder X-ray diffraction pattern of the bis-maleate salt of N,2-dimethyl-6-[7-(2-morpholinoethoxy)quinolin-4-yloxy]benzofuran-3-carboxamide, polymorph Form III.

Polymorph Form III of the bis-maleate salt of N,2-dimethyl-6-[7-(2-morpholinoethoxy)quinolin-4-yloxy]benzofuran-3-carboxamide is a hydrate and can be produced, for example, by dissolving bis-maleate Form I in a solvent such as water after which the hydrated bis-maleate Form III can then be precipitated out. bis-maleate Form III can also be prepared by dissolving bis-maleate Form I in a suitable solvent, such as acetonitrile, followed by seeding with bis-maleate Form III to obtain the conversion of Form I to Form III. The powder X-ray diffraction (PXRD) pattern of bis-maleate Form III is shown in FIG. 6, with corresponding tabulated data shown in Table 3.

TABLE 3

PXRD data tabulation for polymorph Form III of the bis-maleate salt of N,2-dimethyl-6-[7-(2-morpholinoethoxy)quinolin-4-yloxy]benzofuran-3-carboxamide.

| 2θ (°) | D value | Intensity (counts) |
|---|---|---|
| 6.4 | 13.7 | 9.8 |
| 8.3 | 10.6 | 5.1 |
| 9.0 | 9.8 | 5.0 |
| 9.6 | 9.2 | 8.0 |
| 11.9 | 7.4 | 6.0 |
| 12.7 | 7.0 | 15.5 |
| 14.4 | 6.2 | 10.0 |
| 14.9 | 6.0 | 12.3 |
| 16.3 | 5.4 | 8.1 |
| 17.4 | 5.1 | 11.3 |
| 20.1 | 4.4 | 10.6 |
| 21.3 | 42 | 30.3 |

TABLE 3-continued

PXRD data tabulation for polymorph Form III of the bis-maleate salt of N,2-dimethyl-6-[7-(2-morpholinoethoxy)quinolin-4-yloxy]benzofuran-3-carboxamide.

| 2θ (°) | D value | Intensity (counts) |
|---|---|---|
| 24.3 | 3.7 | 9.3 |
| 25.1 | 3.6 | 7.4 |
| 25.9 | 3.4 | 16.9 |
| 27.9 | 3.2 | 11.0 |

Figure 7:
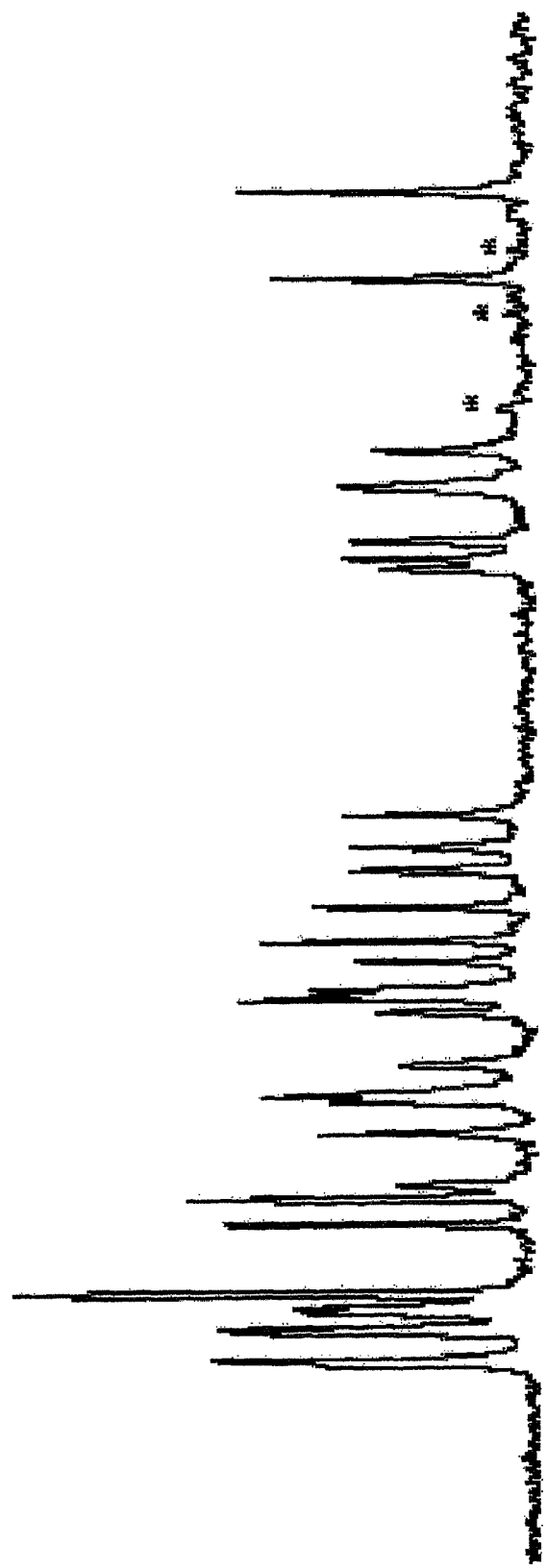
FIG. 7 shows a solid state NMR spectrum of the bis-maleate salt of N,2-dimethyl-6-[7-(2-morpholinoethoxy)quinolin-4-yloxy]benzofuran-3-carboxamide, polymorph Form III.

The solid state NMR spectrum of bis-maleate Form III is shown in FIG. 7, with corresponding tabulated carbon chemical shift data shown in Table 4.

TABLE 4

Carbon chemical shifts of polymorph Form III of the bis-maleate salt of N,2-dimethyl-6-[7-(2-morpholinoethoxy)quinolin-4-yloxy]benzofuran-3-carboxamide.

| Peak Number[a] | [13]C Chemical Shifts[b] [ppm] | Intensity[c] [Arbitrary Units] |
|---|---|---|
| 1 | 172.5 | 6.8 |
| 2 | 168.8 | 6.5 |
| 3 | 168.1 | 6.7 |
| 4 | 166.1 | 4.8 |
| 5 | 165.4 | 5.0 |
| 6 | 163.6 | 12.0 |
| 7 | 154.4 | 6.5 |
| 8 | 150.9 | 7.3 |
| 9 | 149.2 | 2.8 |
| 10 | 142.2 | 4.5 |
| 11 | 137.7 | 4.2 |
| 12 | 137.0 | 5.6 |
| 13 | 132.8 | 2.7 |
| 14 | 125.8 | 3.1 |
| 15 | 124.0 | 6.2 |
| 16 | 123.3 | 4.6 |
| 17 | 122.6 | 4.6 |
| 18 | 119.0 | 3.6 |
| 19 | 116.1 | 5.7 |
| 20 | 111.4 | 4.5 |
| 21 | 106.4 | 3.7 |
| 22 | 103.3 | 3.7 |
| 23 | 99.2 | 3.9 |
| 24 | 65.9 | 3.0 |
| 25 | 64.5 | 3.8 |
| 26 | 62.1 | 3.7 |
| 27 | 55.0 | 3.4 |
| 28 | 54.5 | 3.9 |
| 29 | 49.9 | 3.2 |
| 30 | 26.5 | 5.4 |
| 31 | 14.8 | 6.1 |

[a]Peak numbers lists all peaks by descending chemical shifts.
[b]Referenced to external sample of solid phase adamantane at 29.5 ppm.
[c]Defined as peak heights. Intensities can vary depending on the actual setup of the CPMAS experimental parameters. CPMAS intensities are not necessarily quantitative.

Figure 8:
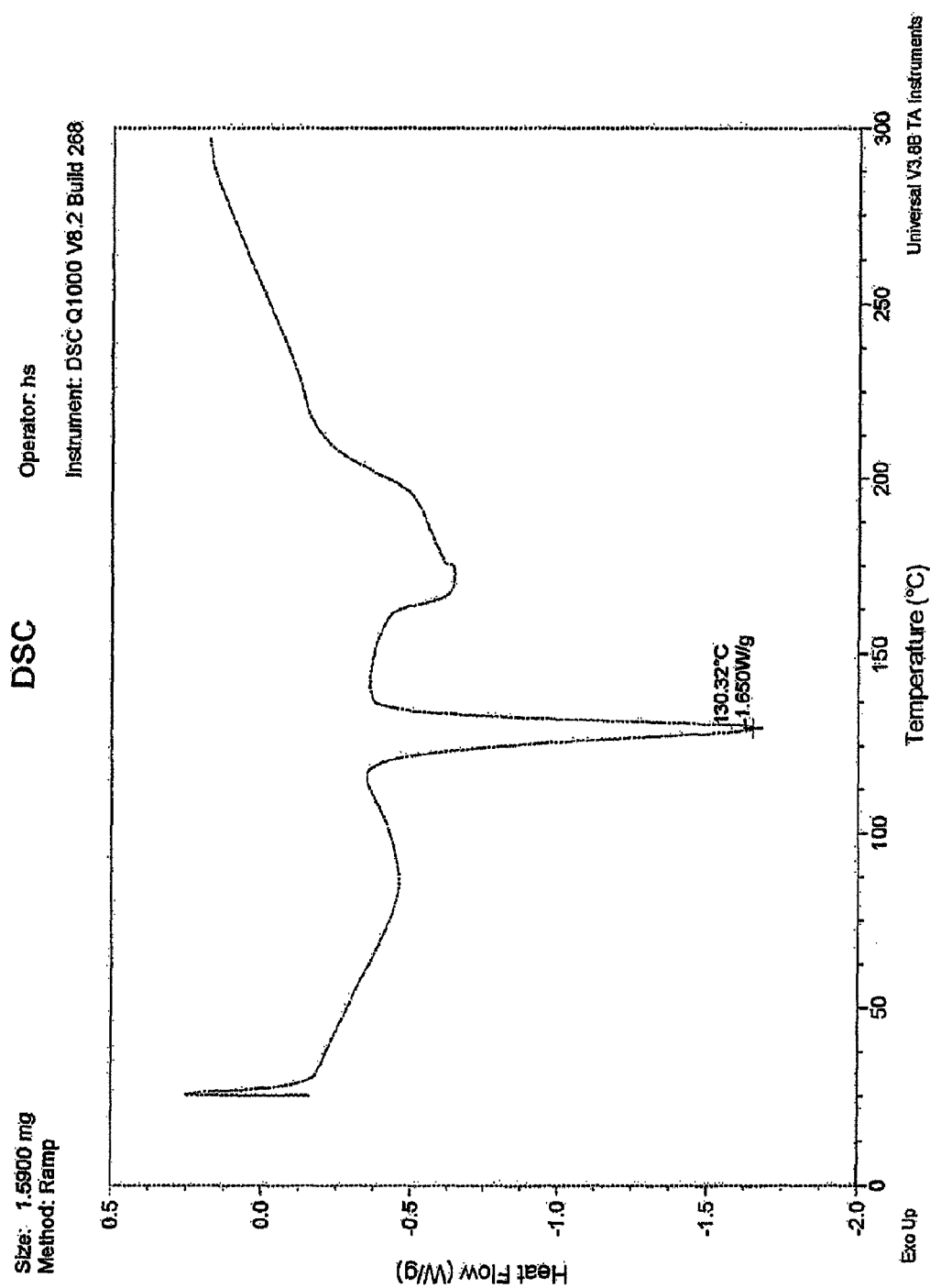
FIG. 8 shows a differential scanning calorimetery (DSC) thermogram of the bis-maleate salt of N,2-dimethyl-6-[7-(2-morpholinoethoxy)quinolin-4-yloxy]benzofuran-3-carboxamide, polymorph Form III.
Figure 9:
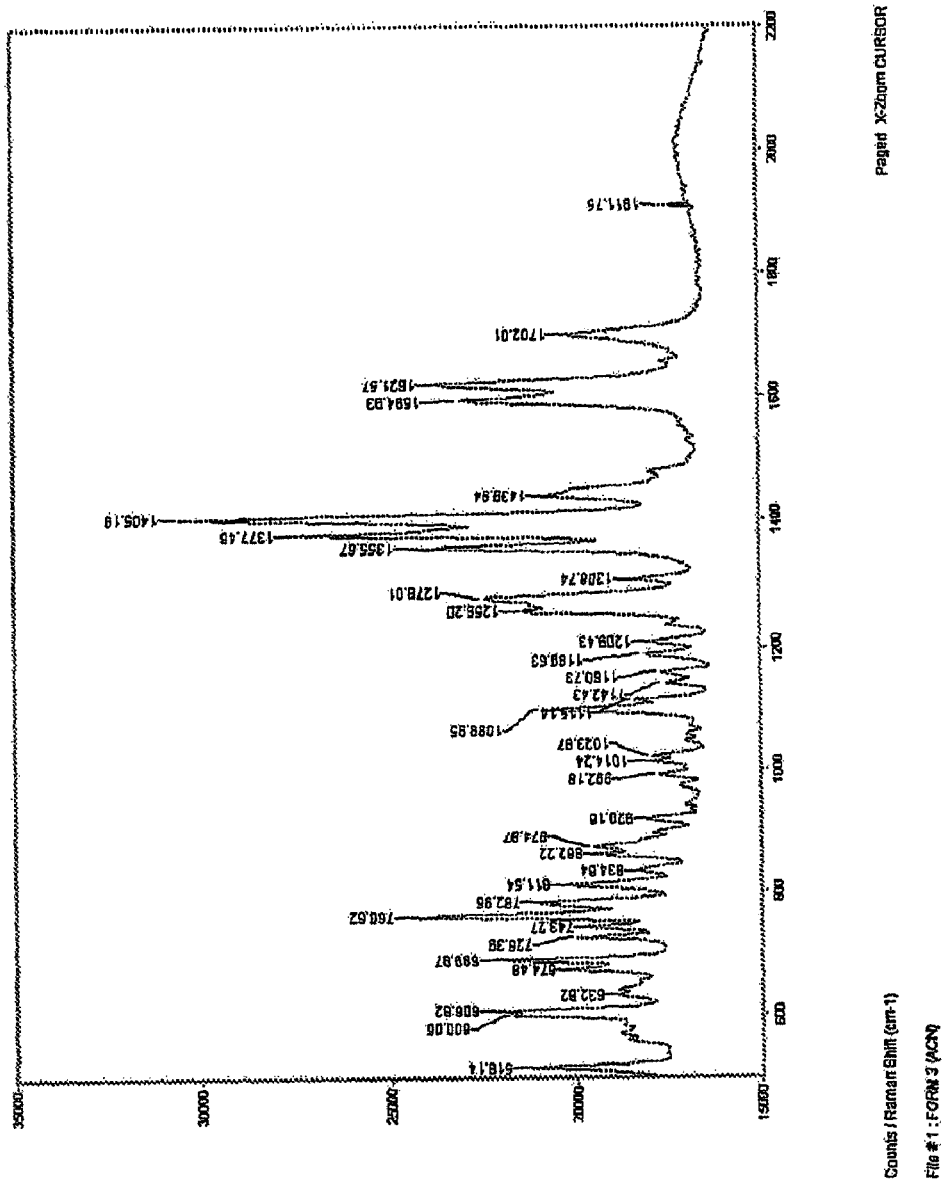
FIG. 9 shows a Raman spectrograph of the bis-maleate salt of N,2-dimethyl-6-[7-(2-morpholinoethoxy)quinolin-4-yloxy]benzofuran-3-carboxamide, polymorph Form III.
Figure 10:
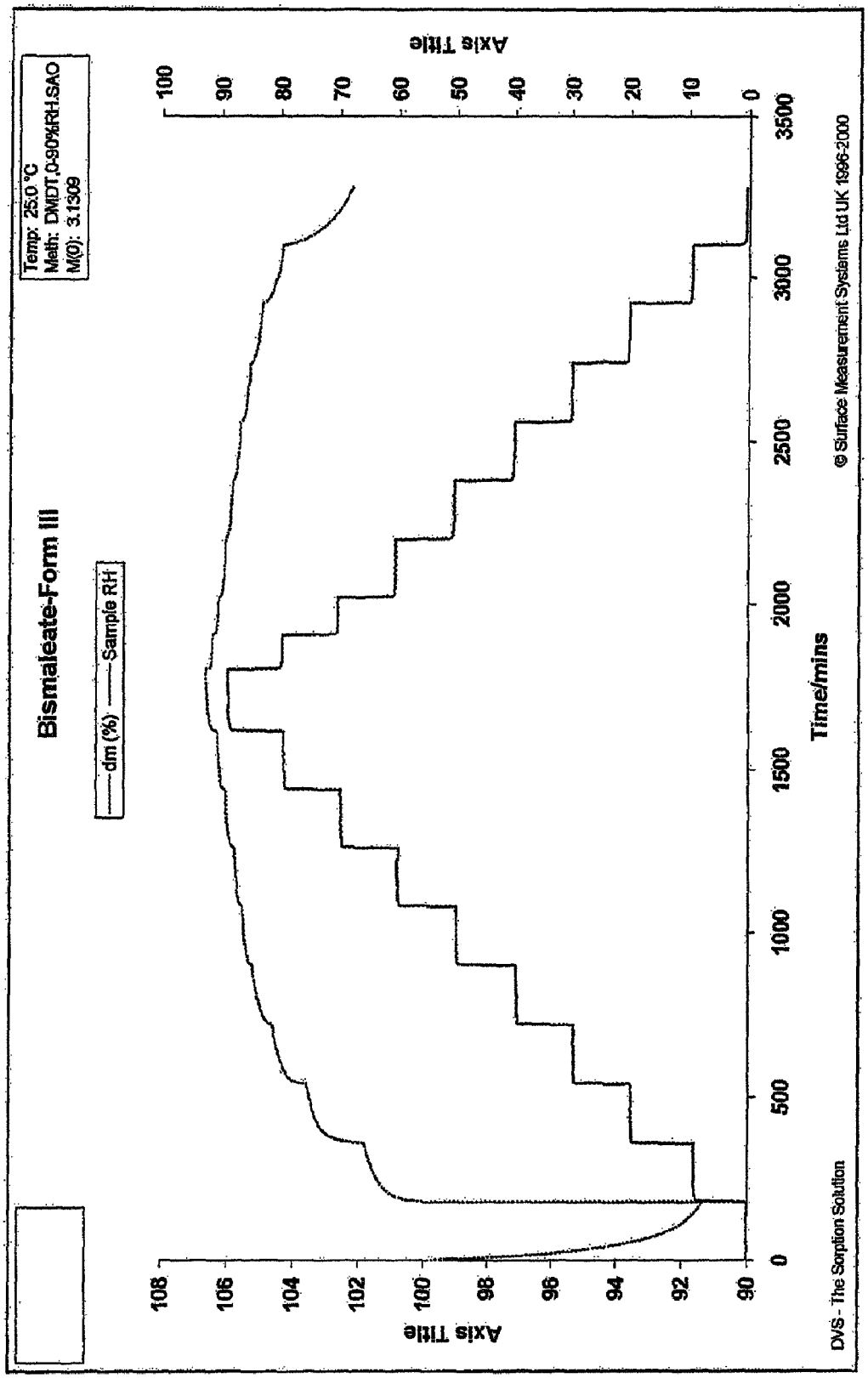
FIG. 10 shows a dynamic vapor sorption profile of the bis-maleate salt of N,2-dimethyl-6-[7-(2-morpholinoethoxy)quinolin-4-yloxy]benzofuran-3-carboxamide, polymorph Form III.

The DSC thermogram for bis-maleate Form III is shown in FIG. 8, the Raman spectrograph for bis-maleate Form III is shown in FIG. 9, and the dynamic vapor sorption profile for bis-maleate Form III is shown in FIG. 10.

The solid state stability of the polymorphic forms of the bis-maleate salt of N,2-dimethyl-6-[7-(2-morpholinoethoxy)quinolin-4-yloxy]benzofuran-3-carboxamide are shown below in Table 5.

TABLE 5

Solid state stability of the bis-maleate salt of N,2-dimethyl-6-[7-(2-morpholinoethoxy)quinolin-4-yloxy]benzofuran-3-carboxamide, Form I and III at 40° C./75% RH

| Samples | T (0) | T (1 week) | | T (4 week) | | T (6 week) | |
|---|---|---|---|---|---|---|---|
| | | open | close | open | close | open | close |
| Bis-maleate Form I | 99.9% | 99.9% | 99.9% | 99.9% | 99.9% | 99.8% | 99.9% |
| | Form I | Form I | Form I | Form I | Form I | Form I | Form I |
| Bis-maleate Form III | 99.9% | — | — | — | — | — | 99.9% |
| | Form III | Form III | Form III | Form III | — | Form III |

The water solubility of the polymorphic Forms I and III of the bis-maleate salt of N,2-dimethyl-6-[7-(2-morpholinoethoxy)quinolin-4-yloxy]benzofuran-3-carboxamide are shown below in Table 6.

TABLE 6

Water solubility of bis-maleate salts of N,2-dimethyl-6-[7-(2-morpholinoethoxy)quinolin-4-yloxy]benzofuran-3-carboxamide.

| Salt form | Solubility mg/mL |
|---|---|
| Bis-maleate Form I | At least 150 (pH 3.6) |
| Bis-maleate Form III | At least 30 (pH 3.8) |

Amorphous bis-maleate

Figure 34:
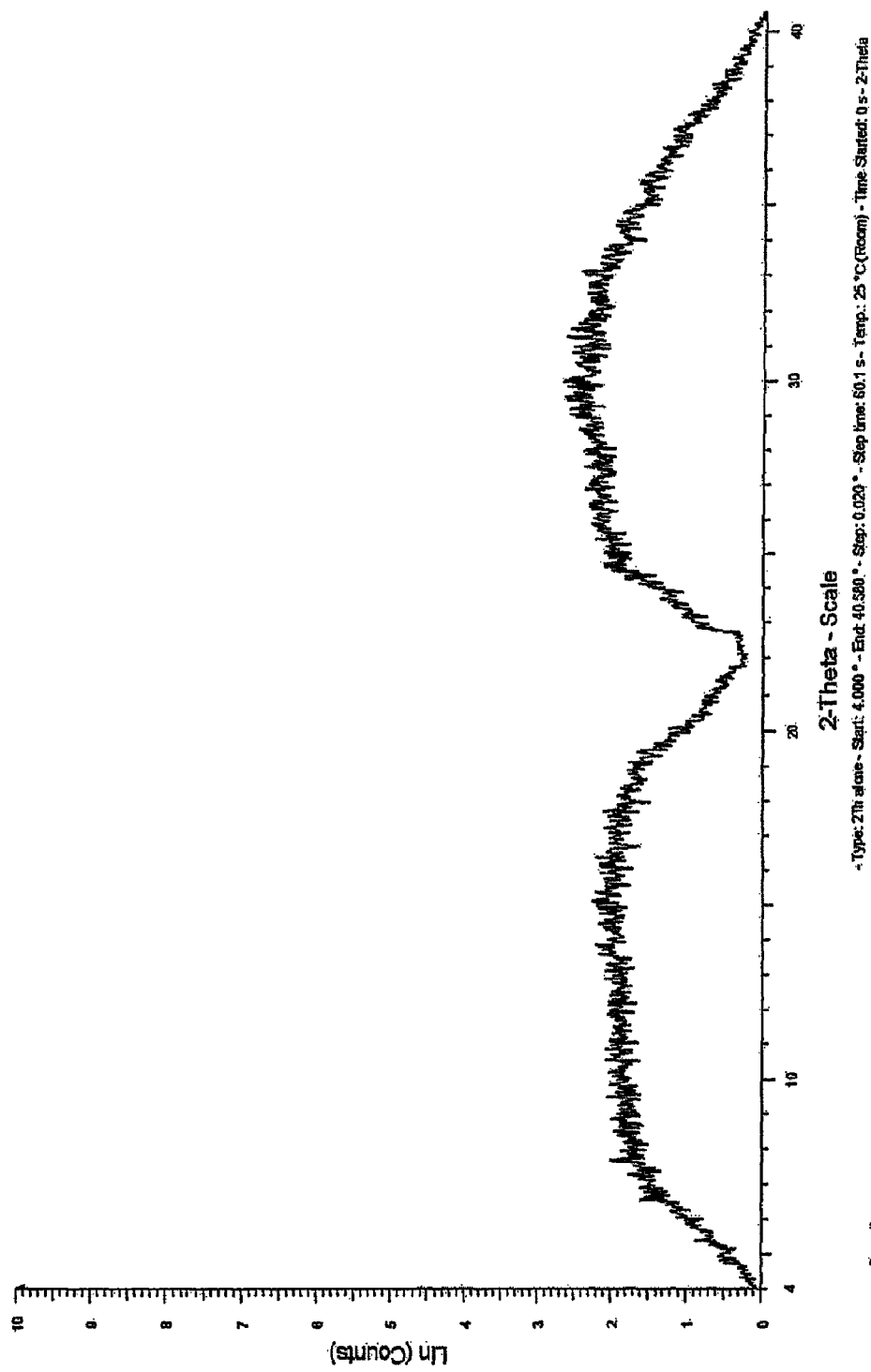
FIG. 34 shows a powder X-ray diffraction pattern of the bis-maleate salt of N,2-dimethyl-6-[7-(2-morpholinoethoxy)quinolin-4-yloxy]benzofuran-3-carboxamide in an amorphous form.

As indicated in Example 11, an amorphous form of the bis-maleate salt of N,2-dimethyl-6-[7-(2-morpholinoethoxy)quinolin-4-yloxy]benzofuran-3-carboxamide can also be made by dissolving the bis-maleate salt in an appropriate solvent such as methanol, followed by drying (e.g. at about 40° C.) to obtain the solid amorphous form. The powder X-ray diffraction pattern for the amorphous bis-maleate form is shown in FIG. 34.

Crystalline bis-HBr Salt

Figure 29:
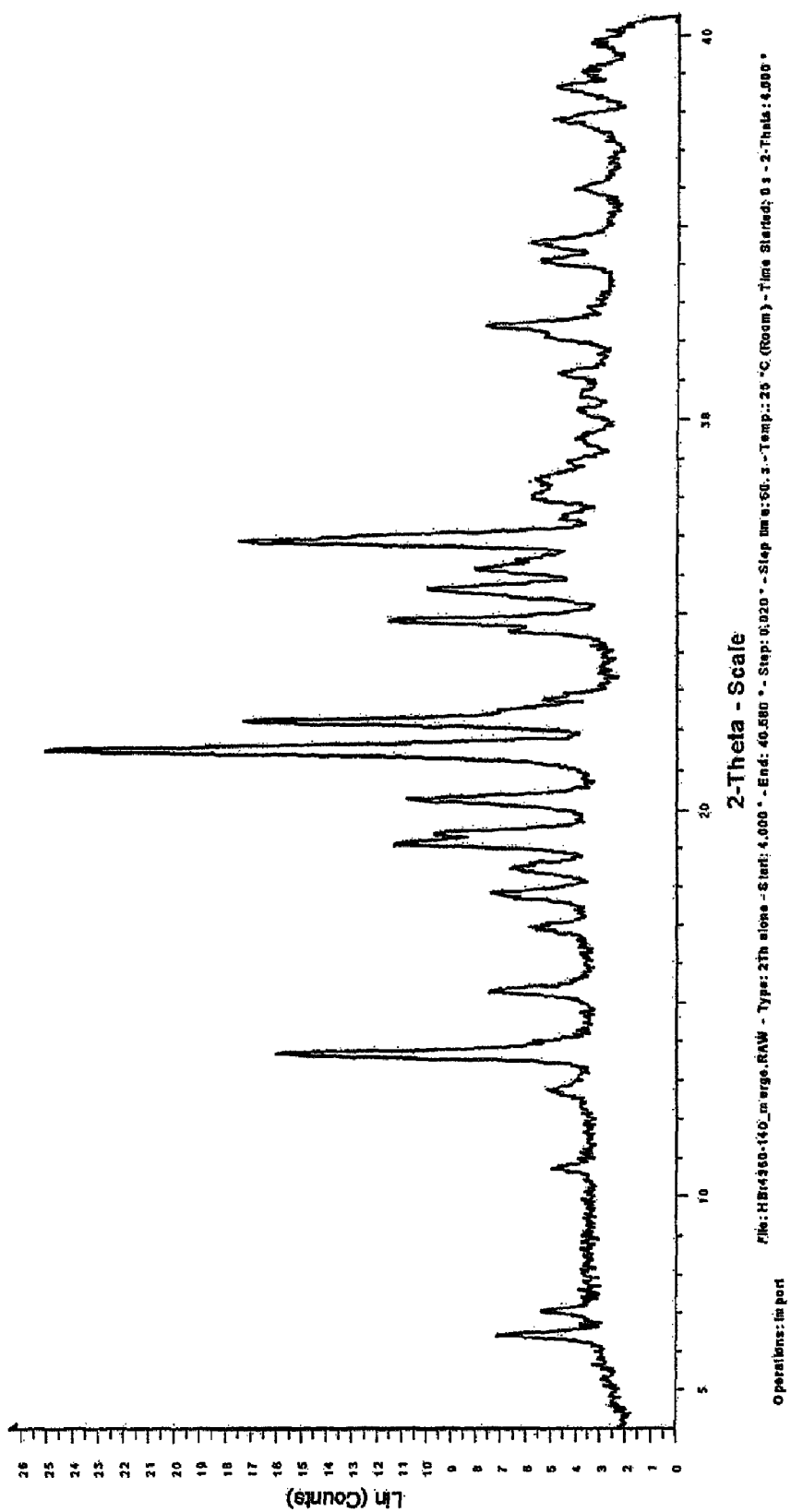
FIG. 29 shows a powder X-ray diffraction pattern of the bis-HBr salt of N,2-dimethyl-6-[7-(2-morpholinoethoxy)quinolin-4-yloxy]benzofuran-3-carboxamide polymorph Form I.
Figure 30:
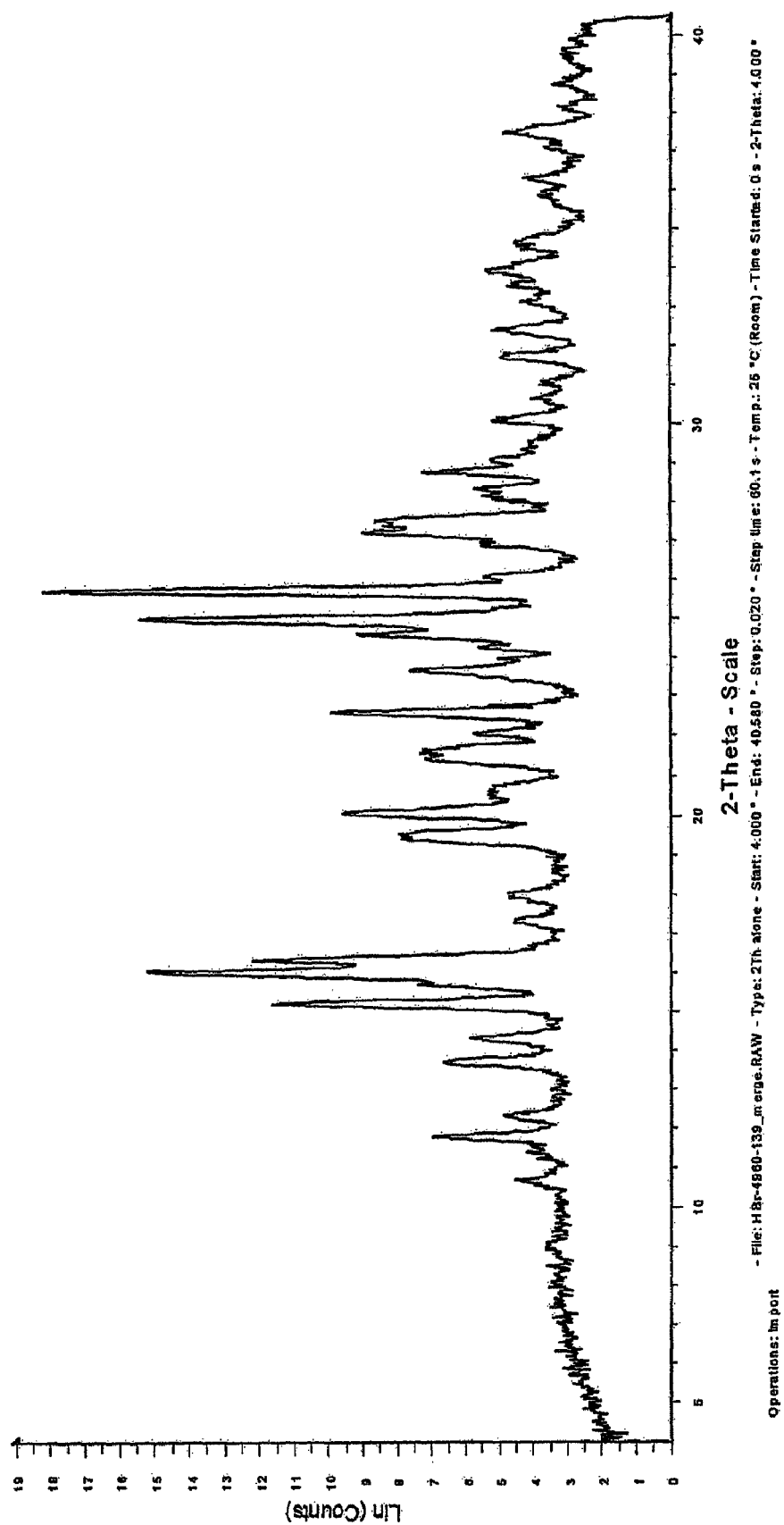
FIG. 30 shows a powder X-ray diffraction pattern of the bis-HBr salt of N,2-dimethyl-6-[7-(2-morpholinoethoxy)quinolin-4-yloxy]benzofuran-3-carboxamide polymorph Form II.
Figure 31:
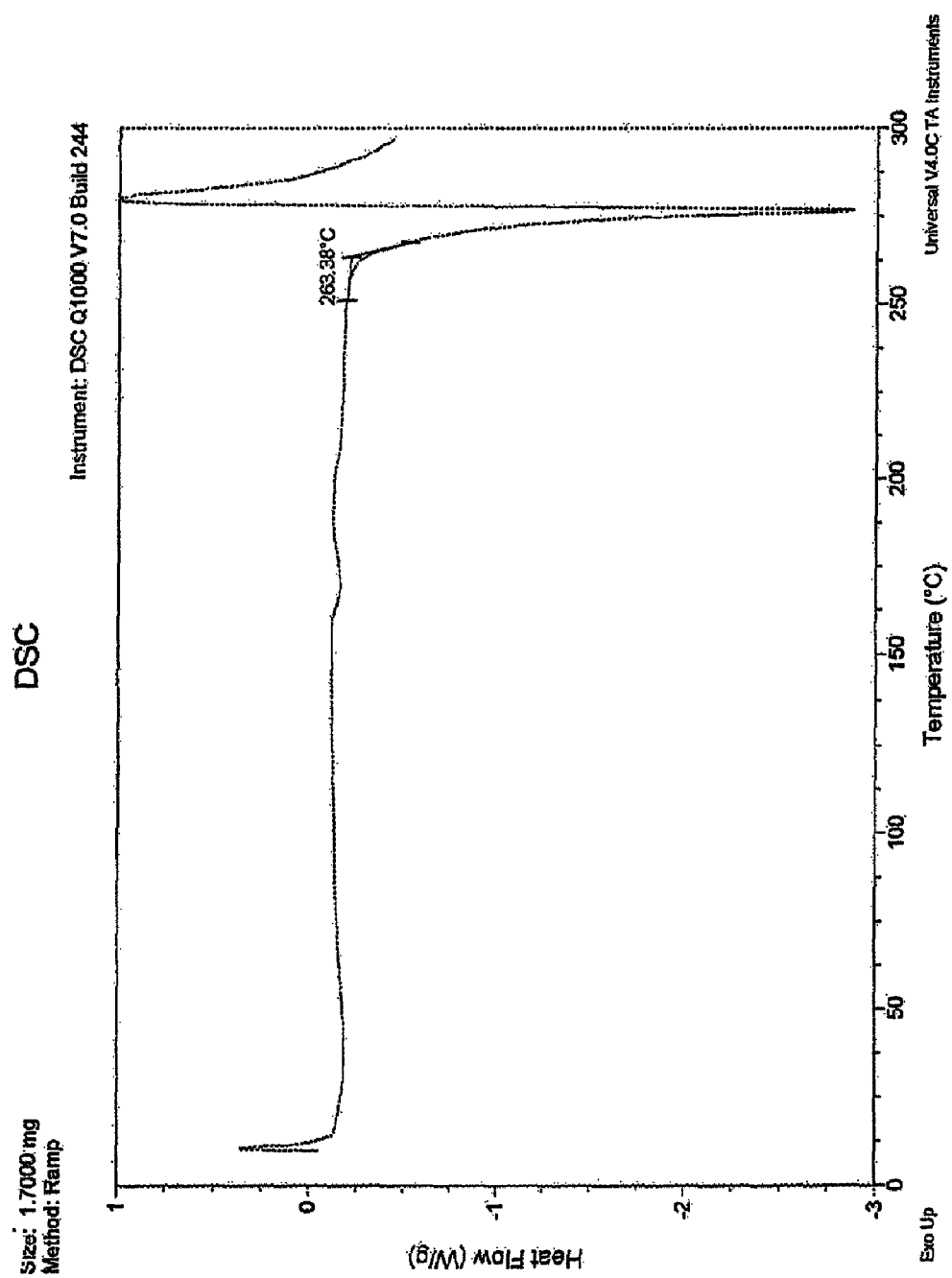
FIG. 31 shows a differential scanning calorimetery (DSC) thermogram of the bis-HBr salt of N,2-dimethyl-6-[7-(2-morpholinoethoxy)quinolin-4-yloxy]benzofuran-3-carboxamide, Form I.
Figure 32:
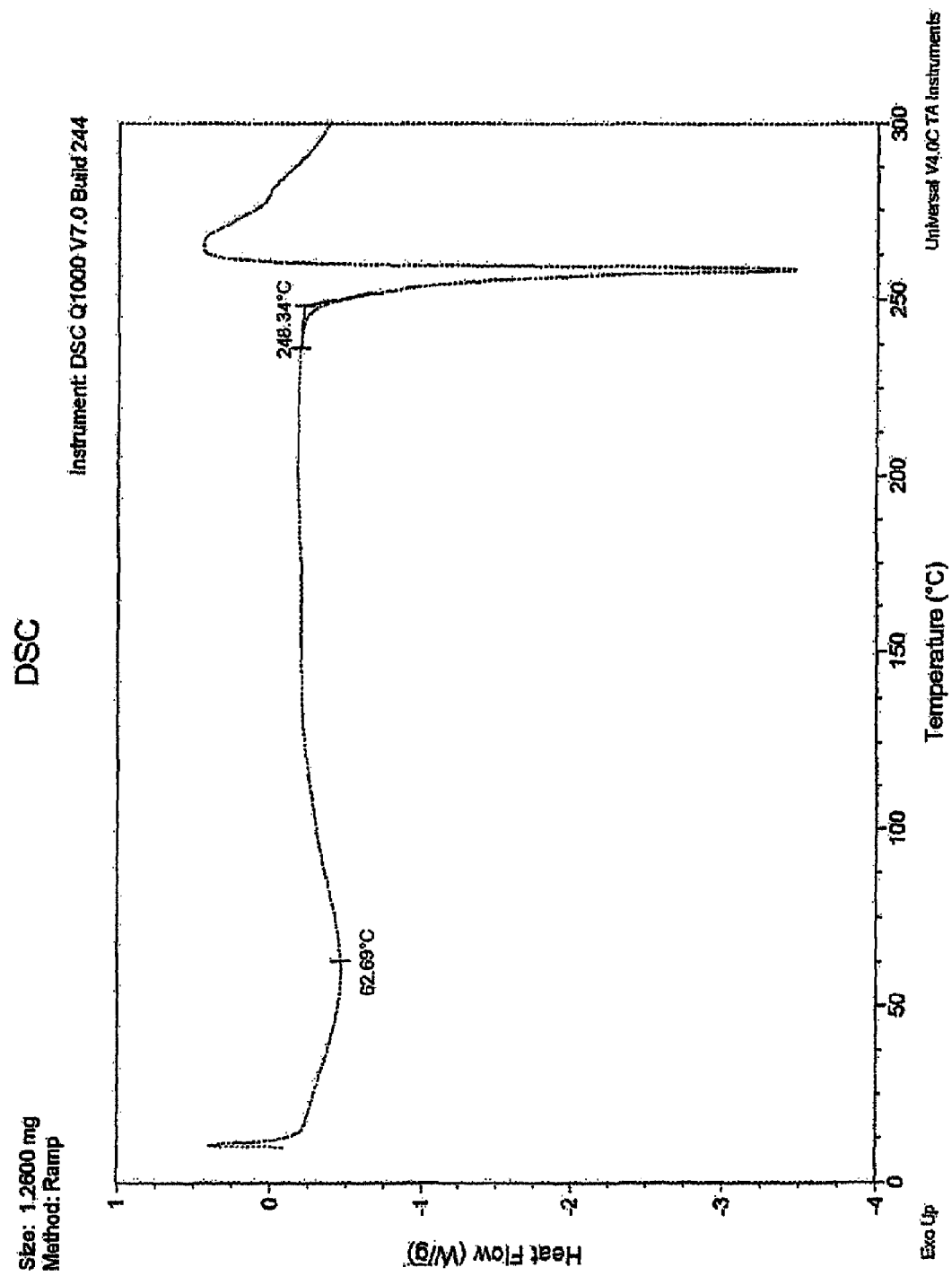
FIG. 32 shows a differential scanning calorimetery (DSC) thermogram of the bis-HBr salt of N,2-dimethyl-6-[7-(2-morpholinoethoxy)quinolin-4-yloxy]benzofuran-3-carboxamide, Form II.
Figure 33:
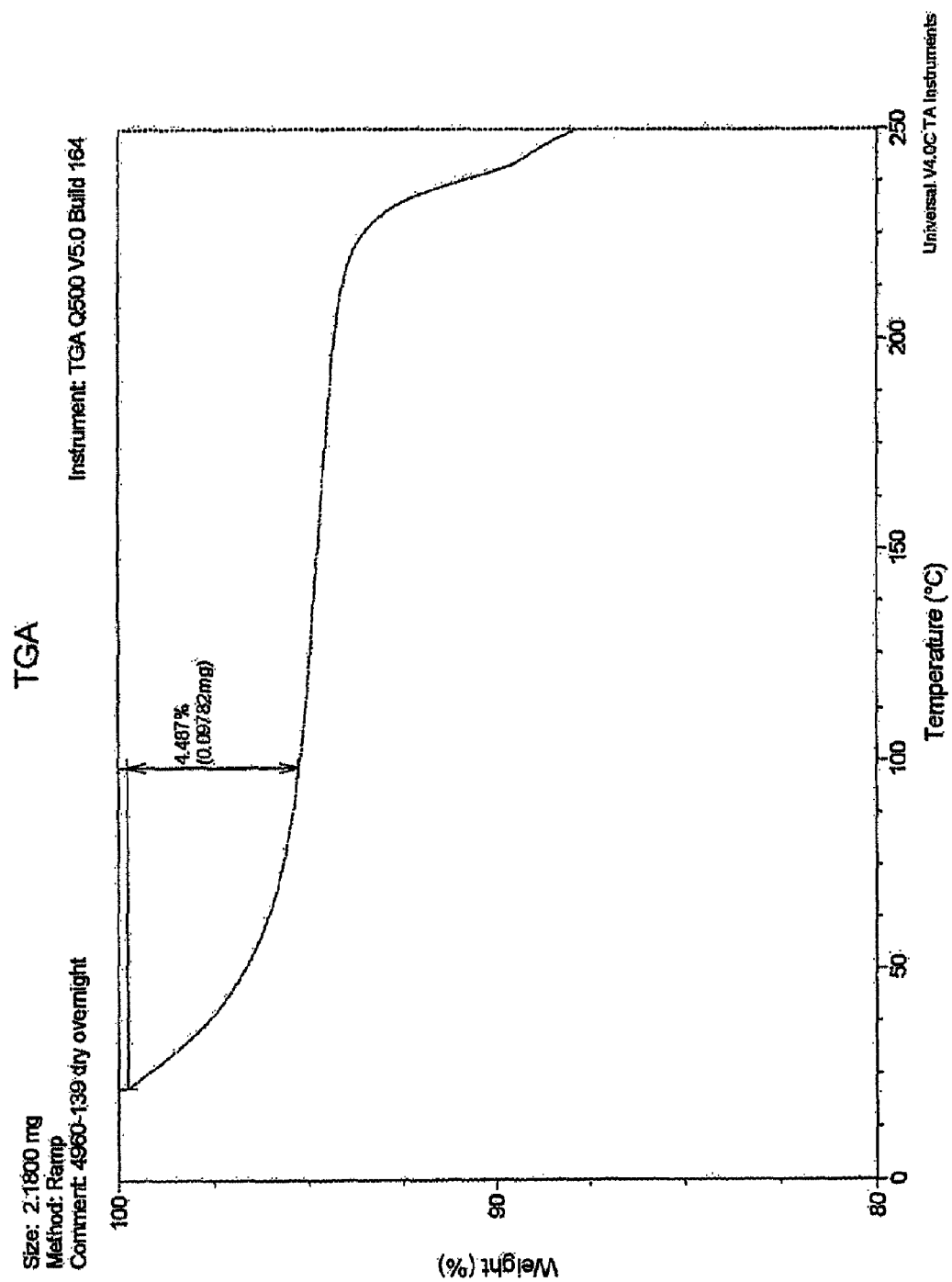
FIG. 33 shows a thermogravimetric analysis (TGA) profile for the bis-HBr salt of N,2-dimethyl-6-[7-(2-morpholinoethoxy)quinolin-4-yloxy]benzofuran-3-carboxamide, Form II.

The bis-hydrobromide salt (bis-HBr) of N,2-dimethyl-6-[7-(2-morpholinoethoxy)quinolin-4-yloxy]benzofuran-3-carboxamide can be produced with good crystallinity, for example, by dissolving the free base compound in any suitable solvent, such as $CH_2Cl_2$, THF, acetonitrile, ethyl acetate, methanol, or ethanol at an elevated temperature (e.g. ~75° C.), followed by the addition of hydrobromic acid in a suitable solvent such as acetonitrile. The solid crystalline material can then be obtained by cooling the solution to a room temperature at a rate of about 20° C. per hour. As shown in Examples 9 and 10, at least two different crystalline forms of the bis-HBr salt can be obtained. One polymorphic form of the bis-HBr salt is an anhydrous form with an on-set melting temperature of 263° C. (see FIG. 31) and is designated as bis-HBr Form I. A second polymorphic form is a solvate and is designated as bis-HBr Form II. The powder X-ray diffraction pattern for bis-HBr Form I is shown in FIG. 29, while the DSC thermogram for bis-HBr Form I is shown in FIG. 31. The powder X-ray diffraction pattern for bis-HBr Form II is shown in FIG. 30, the DSC thermogram for bis-HBr Form II is shown in FIG. 32, and a thermogravimetric profile for bis-HBr Form II is shown in FIG. 33. bis-HBr Form II is a solvate form with a desolvation temperature of 63° C. (see FIG. 32). The on-set melting point of bis-HBr Form II is 248° C. (see FIG. 32). The thermogravimetric analysis (TGA) of bis-HBr Form II shows a weight loss of 4.5% upon heating to 100° C. (see FIG. 33). Karl-Fisher titration was performed on bis-HBr Form II to determine its water content. The result indicated a water content of 4.1%. Therefore bis-HBr Form II was identified as a hydrate form.

The solid state stability of the polymorphic forms of the bis-HBr salt of N,2-dimethyl-6-[7-(2-morpholinoethoxy)quinolin-4-yloxy]benzofuran-3-carboxamide are shown below in Table 7.

TABLE 7

Solid state stability of the bis-HBr salt of N,2-dimethyl-6-[7-(2-morpholinoethoxy)quinolin-4-yloxy]benzofuran-3-carboxamide, Forms I and II at 40° C./75% RH.

| Samples | T (0) | T (1 week) | | T (4 week) | | T (6 week) | |
|---|---|---|---|---|---|---|---|
| | | open | close | open | close | open | close |
| Bis-HBr Form I | — | — | — | — | — | — | — |
| | | Form 1 | Form I & II | Form 1 | Form II | Form I & II | Form II | Form II |
| Bis-HBr Form II | 98.53% | 98.61% | 98.70% | 98.62% | 98.66% | 98.49% | 98.61% |
| | Form II | Form II | Form II | Form II | Form II | Form II | Form II |

The water solubility of the two polymorphic forms of the bis-HBr salt of N,2-dimethyl-6-[7-(2-morpholinoethoxy) quinolin-4-yloxy]benzofuran-3-carboxamide are shown below in Table 8.

TABLE 8

Water solubility of bis-HBr salts of N,2-dimethyl-6-[7-(2-morpholinoethoxy)quinolin-4-yloxy]benzofuran-3-carboxamide.

| Salts forms | Solubility |
| --- | --- |
| Bis-HBr Form I | >30 mg/ml (pH 3.4) |
| Bis-HBr Form II | >30 mg/ml (pH 3.4) |

Crystalline Free Base

Crystalline forms of the free base compound N,2-dimethyl-6-[7-(2-morpholinoethoxy)quinolin-4-yloxy]benzofuran-3-carboxamide can also be prepared as described in Examples 3 to 8. Six different crystalline forms of free base N,2-dimethyl-6-[7-(2-morpholinoethoxy)quinolin-4-yloxy] benzofuran-3-carboxamide have been identified and characterized as indicated in FIGS. 11 to 28. These six crystalline forms of free base N,2-dimethyl-6-[7-(2-morpholinoethoxy) quinolin-4-yloxy]benzofuran-3-carboxamide are designated as free base polymorph Forms 1 to 6. Free base polymorph Forms 1 and 4 are hydrates, whereas free base Forms 2, 3, 5, and 6 are anhydrous.

Amorphous Free Base

Figure 35:
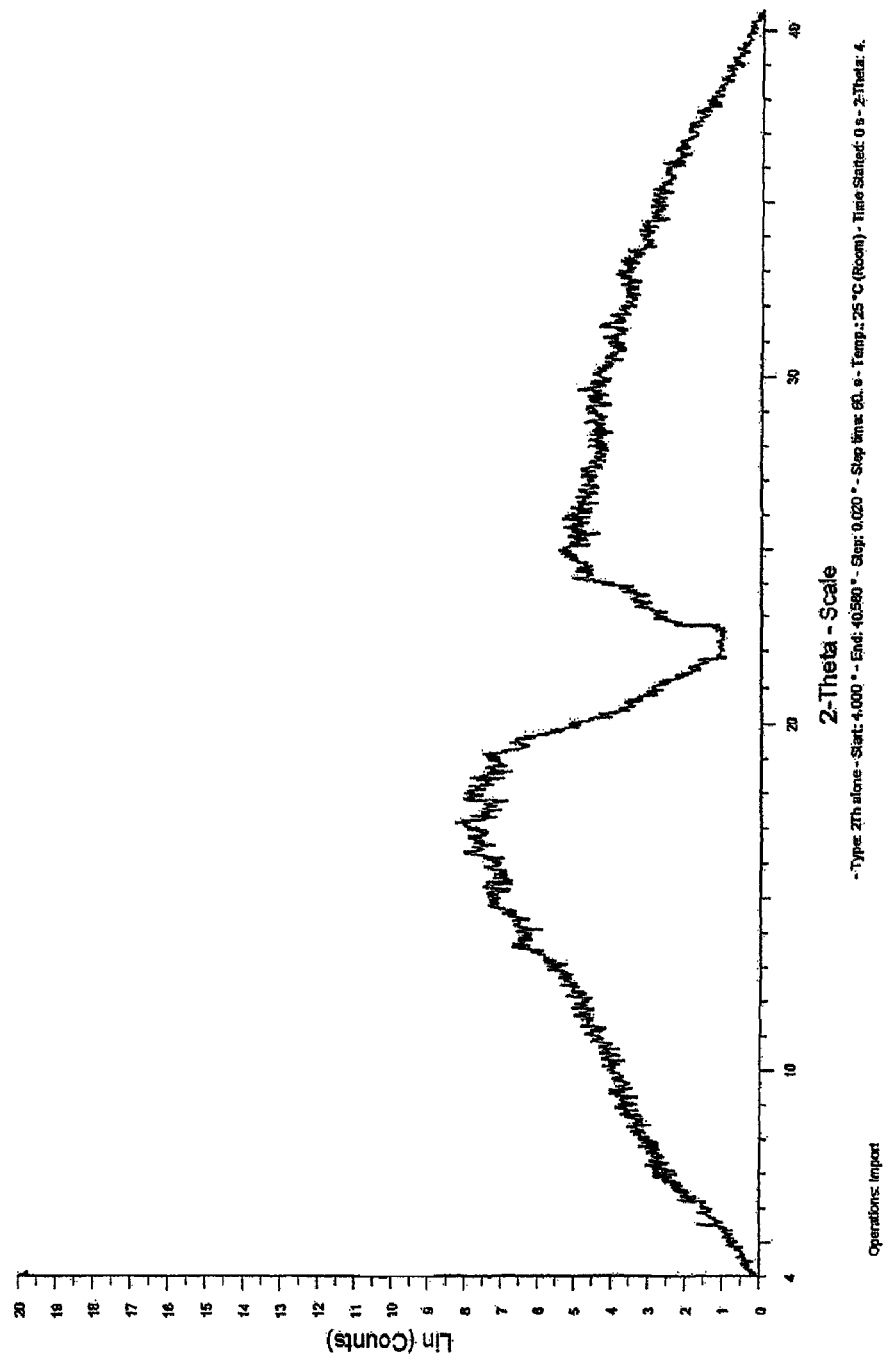
FIG. 35 shows a powder X-ray diffraction pattern of free base N,2-dimethyl-6-[7-(2-morpholinoethoxy)quinolin-4-yloxy]benzofuran-3-carboxamide in an amorphous form.

As indicated in Example 12, an amorphous form of the free base of N,2-dimethyl-6-[7-(2-morpholinoethoxy)quinolin-4-yloxy]benzofuran-3-carboxamide can also be made by dissolving the free base in an appropriate solvent such as an ethanol/methanol mixture, followed by drying (e.g. at about 40° C.) to obtain the solid amorphous form. The powder X-ray diffraction pattern for the amorphous free base form is shown in FIG. 35.

The present invention also relates to pharmaceutical compositions comprising the various physical forms of N,2-dimethyl-6-[7-(2-morpholinoethoxy)quinolin-4-yloxy]benzofuran-3-carboxamide as described herein. Pharmaceutical compositions of the present invention may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

EXAMPLES

The examples and preparations provided below further illustrate and exemplify particular aspects of embodiments of the invention. It is to be understood that the scope of the present invention is not limited in any way by the scope of the following examples.

Methods and Materials

Differential Scanning Calorimetry (DSC): DSC measurements, shown in FIGS. 3, 8, 23 to 28, 31, and 32 were carried out using a Q1000, Themal Analysis Instruments. Sample weight ranged from 1 to 2 mg in a hermetically sealed aluminum pan with a pinhole. The samples were equilibrated to 30° C., followed by an isothermal hold for 3 minutes and then ramped to 200 or 300° C. at a scan rate of 10° C./min. Dry nitrogen was used as the purge gas.

Powder X-ray Diffraction (PXRD): PXRD data for FIGS. 1, 6, 11 to 16, 29, 30, 34, and 35 were collected according to the following protocol. A sample (2 mg) was placed on a microscopic slide with zero background. The sample was then placed in a Discover D8 (Bruker AXS Instruments) equipped with a GADDS detector. The system used a copper X-ray source maintained at 40 kV and 40 mA to provide CUα1 emission at 1.5406 angstroms. Data were collected from 4 to 40° 2θ using a step scan of 0.02° with a step time of 60.1 seconds. Diffraction peaks are typically measured at a sensitivity of ±0.1 degrees (2θ).

Solid state NMR data shown in FIGS. 2 and 7 were collected according to the following protocol. Approximately 50 mg of the respective samples were tightly packed into a 4 mm ZrO spinner for each sample analyzed. The spectrum were collected at 295 K and ambient pressure on a Bruker-Biospin 4 mm BL triple resonance CPMAS probe positioned into a wide-bore Bruker-Biospin Avance DSX 500 MHz NMR spectrometer. The samples were positioned at the magic angle and spun at 15.0 kHz. The fast spinning speed minimized the intensities of the spinning side bands. The number of scans was adjusted to obtain adequate S/N.

$^{13}$C spectroscopy: The one dimensional $^{13}$C spectrum were collected at ambient conditions using $^{1}$H-$^{13}$C Cross-Polarization Magic Angle Spinning (CPMAS). To optimize the signal sensitivity, the cross-polarization contact time was adjusted to 2.0 ms, and the decoupling field was set to 80 kHz. 512 scans were acquired with a recycle delay of 45 seconds. The spectrum were referenced using an external sample of adamantane with its upfield signal set equal to 29.5 ppm. Chemical shifts are typically measured at a sensitivity of ±0.1 ppm.

The Raman spectral data shown in FIGS. 4, 9, and 17 to 22 were collected using the following protocol. Samples (2 to 5 mg) were transferred on a glass microscope slide and transferred to a Raman microprobe (Kaiser Optical Instruments)

and the focus adjusted on the sample. The Raman shifts were obtained over a wavenumber from 0 to 3500 cm$^{-1}$ using a single accumulation with an exposure of 10 seconds. Raman spectral data are typically measured at a sensitivity of ±1 cm$^{-1}$.

The solid state stabilities as shown in Tables 5 and 7 were measured using the following procedure. A preliminary HPLC method was developed to investigate the stability of the salt forms of compound 1. The HPLC conditions are listed below.

| Buffer: | 25 mM ammonium phosphate buffer (pH 2.5) | |
|---|---|---|
| Organic Modifier: | Acetonitrile | |
| Wavelength; | 210 nm | |
| Column: | Waters Symmetry C18, 4.6 × 150 mm, 5 μm; | |
| Flow rate: | 1.0 mL/minute | |
| Injection Volume: | 10 μL | |
| Run time: | 40 minutes | |
| Column Temp: | Ambient | |
| | Time | % Buffer | ACN (%) |
| Gradient: | 0 | 90 | 10 |
| | 10 | 85 | 15 |
| | 30 | 50 | 50 |
| | 36 | 90 | 10 |
| | 40 | 90 | 10 |

Example 1a

Preparation of bis-maleate Form I

An 8 mL scintillation vial was charged with 0.02 g of N,2-dimethyl-6-[7-(2-morpholinoethoxy)quinolin-4-yloxy]benzofuran-3-carboxamide and 4 mL of ethyl acetate. The vial was stirred and heated to 68° C. and the temperature held for 5 minutes. The maleic acid (11.3 mg, 2.1 equiv.) was added as a solid to the vial. The solution turned milky turning to a slightly turbid solution. After 10 minutes a white solid began to precipitate. Upon precipitation the solution was cooled to room temperature at a rate of 20° C./hour. The vial was placed in a cold bath (or refrigerator at 2° C.) for 2 hours. The solid was collected by vacuum filtration and dried in vacuo (30 inch Hg, 60° C.) overnight. This method produced 0.025 g at a yield of 85%.

The maleic acid can also be added as a solution, instead of as a solid as indicated above.

Example 1b

Preparation of bis-maleate Form I

N,2-dimethyl-6-[7-(2-morpholinoethoxy)quinolin-4-yloxy]benzofuran-3-carboxamide bis-maleate, Form III (0.015 g) was suspended in acetonitrile (2 mL) to obtain a suspension of ~7.5 mg/mL at 25° C. A few seeds of Form I were added to the suspension. The suspension was stirred at 50° C. for 2 days to obtain conversion of Form III to Form I.

Example 2a

Preparation of bis-maleate Form III

N,2-dimethyl-6-[7-(2-morpholinoethoxy)quinolin-4-yloxy]benzofuran-3-carboxamide bis-maleate, Form I (0.26 g) was dissolved in water (2.8 mL) to obtain a solution of ~93 mg/mL at 25° C. Following complete dissolution, the solution was filtered through 0.22 μm pore size filters. The filtered solution was placed at 5° C. on a rotator. N,2-dimethyl-6-[7-(2-morpholinoethoxy)quinolin-4-yloxy]benzofuran-3-carboxamide bis-maleate, Form III was obtained as a precipitate after 12 hours.

Example 2b

Preparation of bis-Maleate Form III

N,2-dimethyl-6-[7-(2-morpholinoethoxy)quinolin-4-yloxy]benzofuran-3-carboxamide bis-maleate Form I (0.015 g) was suspended in acetonitrile (2 mL) to obtain a suspension of ~7.5 mg/mL at 25° C. A few seeds of Form III were added to the suspension. The suspension was stirred at ambient temperature for 3 days to obtain conversion of Form I to Form III.

Example 3

Preparation of Free Base Form 1

Figure 11:
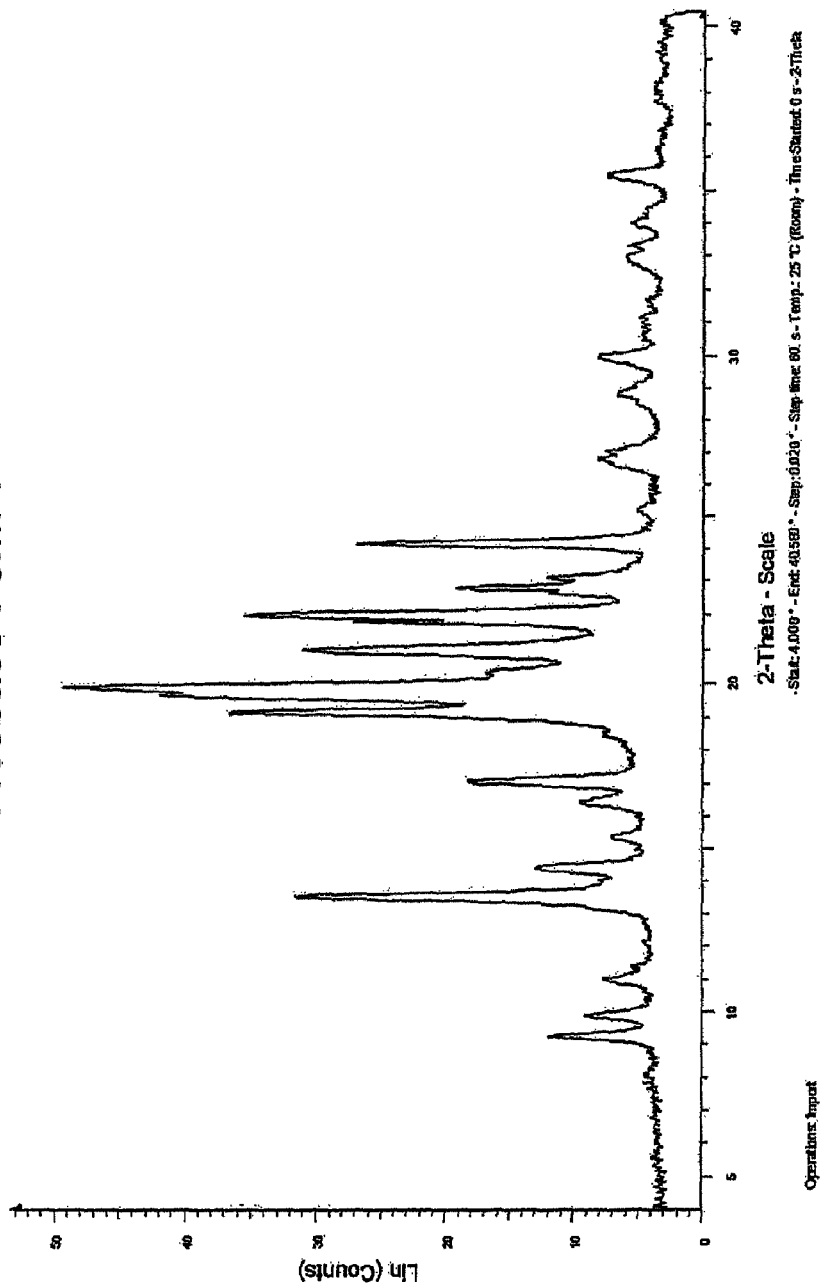
FIG. 11 shows a powder X-ray diffraction pattern of free base N,2-dimethyl-6-[7-(2-morpholinoethoxy)quinolin-4-yloxy]benzofuran-3-carboxamide, polymorph Form 1.
Figure 12:
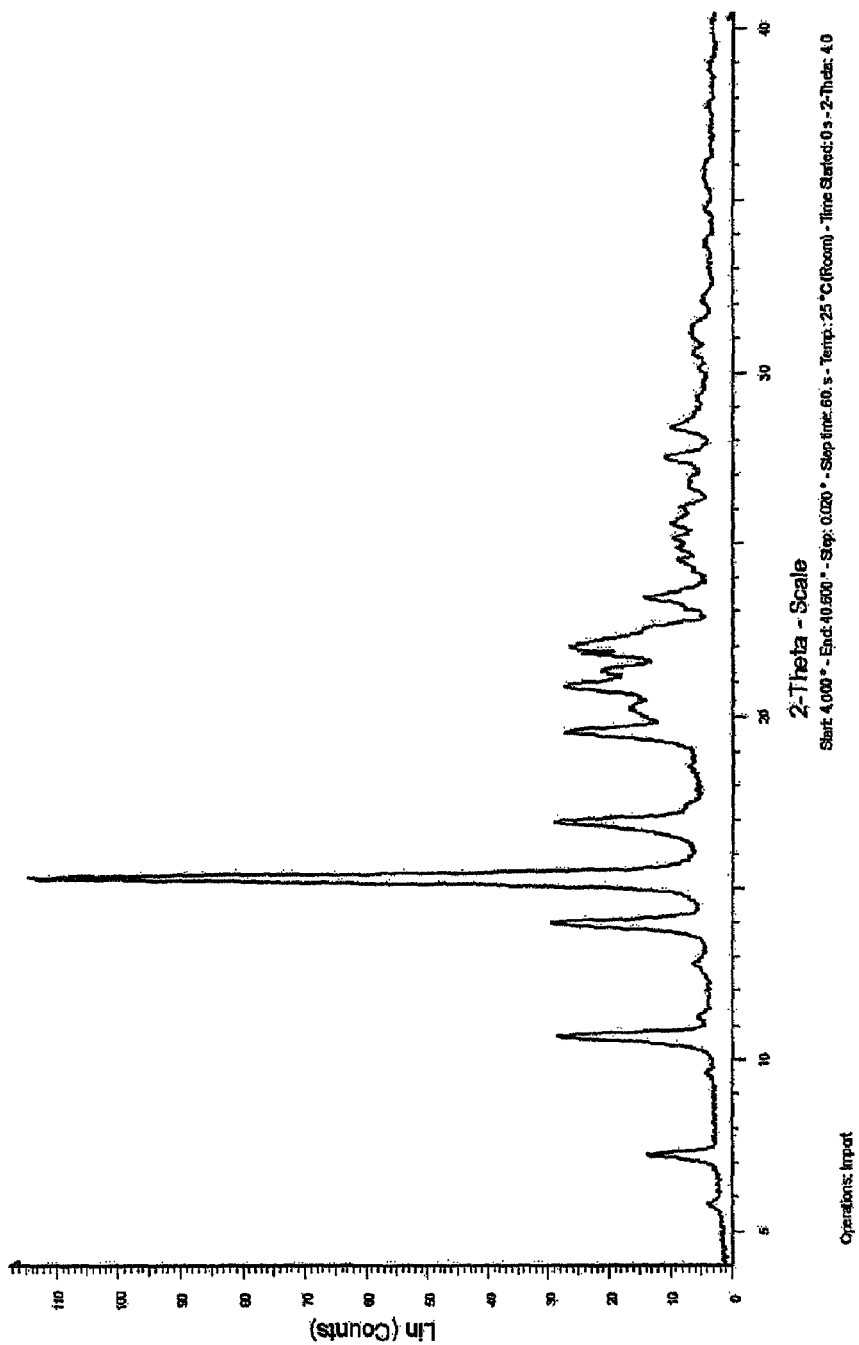
FIG. 12 shows a powder X-ray diffraction pattern of free base N,2-dimethyl-6-[7-(2-morpholinoethoxy)quinolin-4-yloxy]benzofuran-3-carboxamide, polymorph Form 2.
Figure 13:
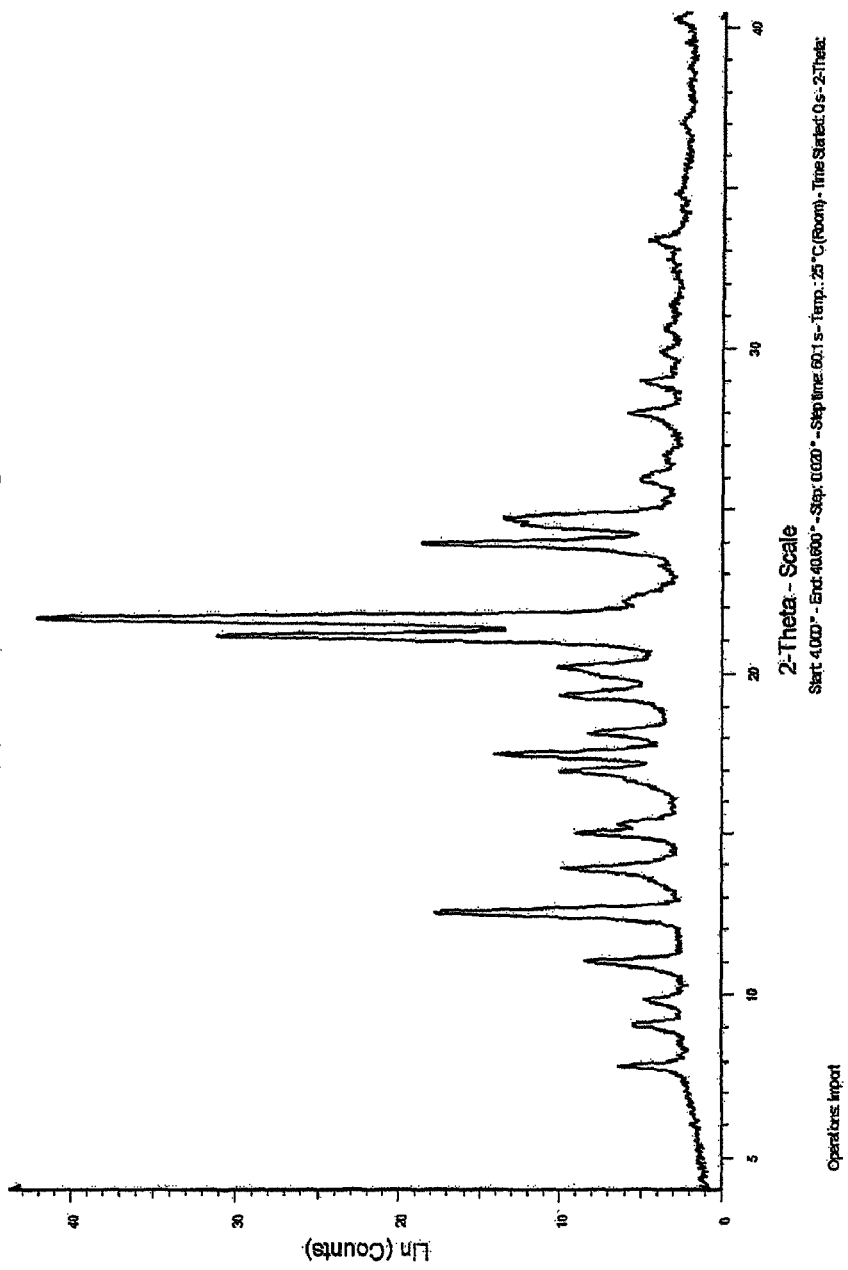
FIG. 13 shows a powder X-ray diffraction pattern of free base N,2-dimethyl-6-[7-(2-morpholinoethoxy)quinolin-4-yloxy]benzofuran-3-carboxamide, polymorph Form 3.
Figure 14:
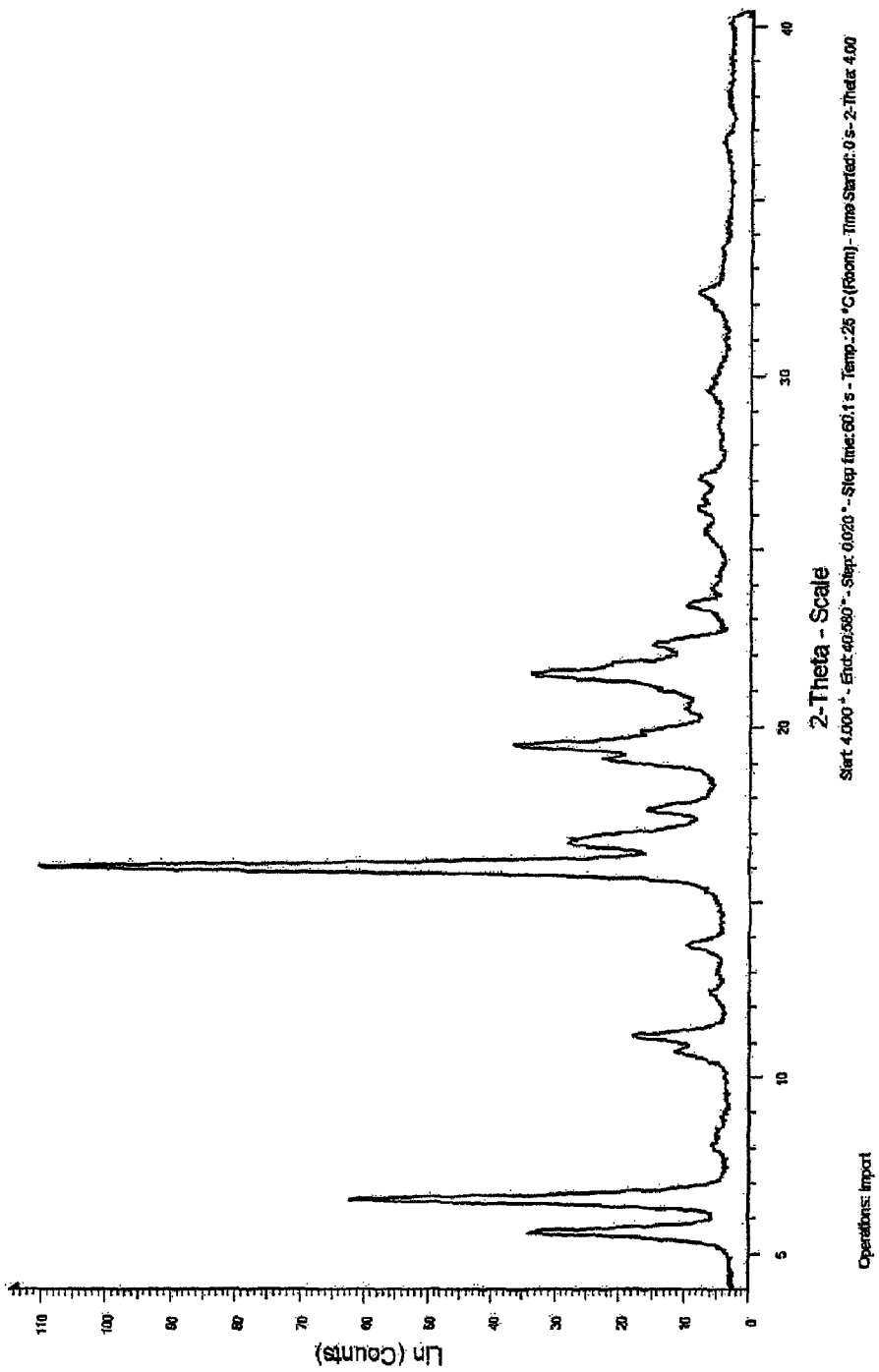
FIG. 14 shows a powder X-ray diffraction pattern of free base N,2-dimethyl-6-[7-(2-morpholinoethoxy)quinolin-4-yloxy]benzofuran-3-carboxamide, polymorph Form 4.
Figure 15:
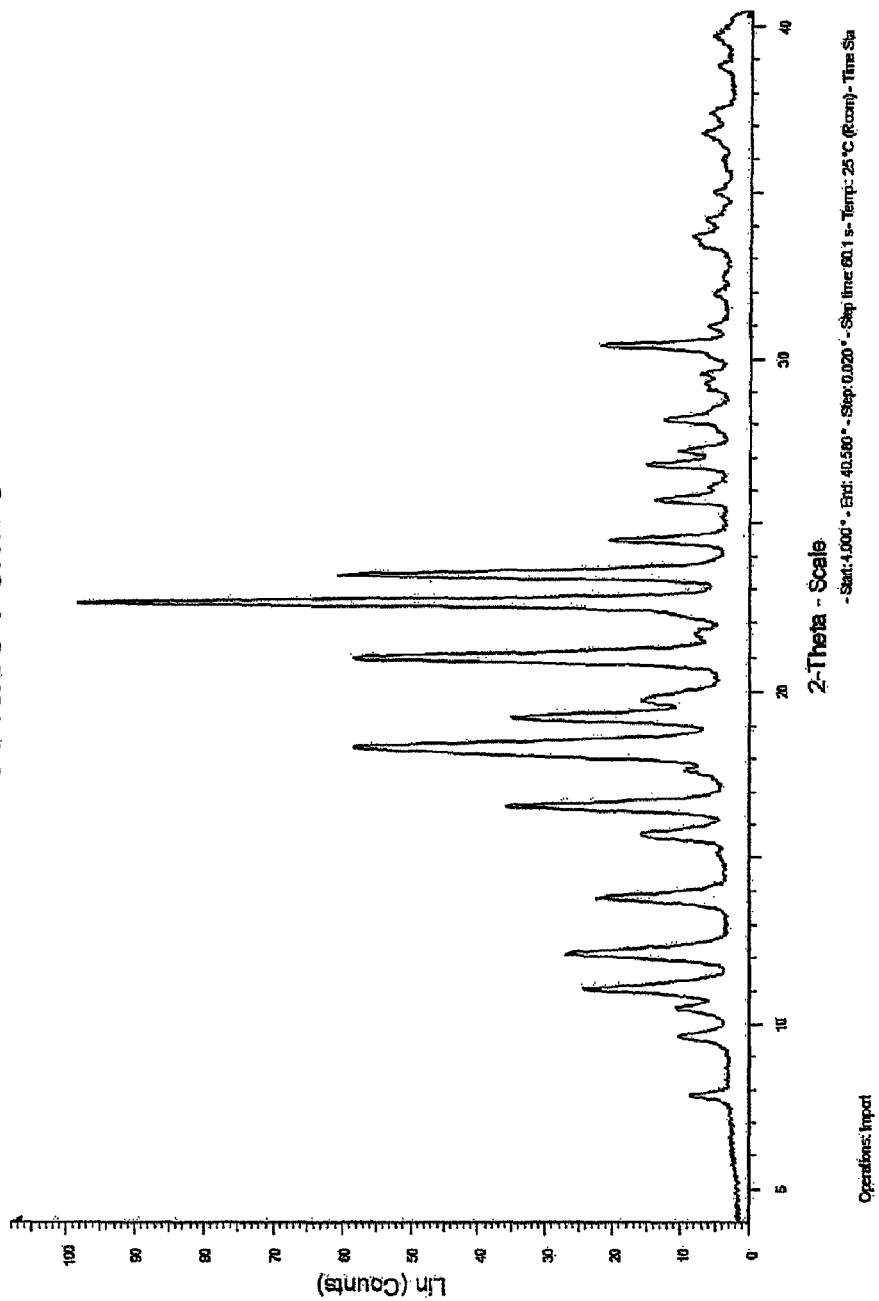
FIG. 15 shows a powder X-ray diffraction pattern of free base N,2-dimethyl-6-[7-(2-morpholinoethoxy)quinolin-4-yloxy]benzofuran-3-carboxamide, polymorph Form 5.
Figure 16:
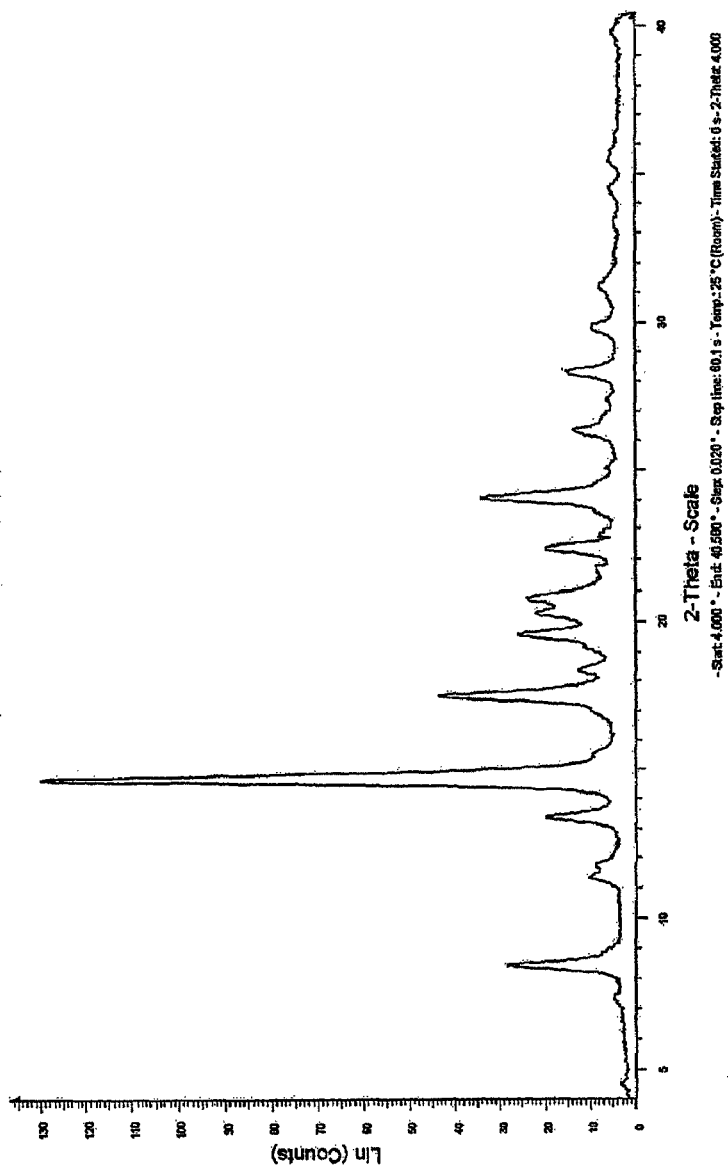
FIG. 16 shows a powder X-ray diffraction pattern of free base N,2-dimethyl-6-[7-(2-morpholinoethoxy)quinolin-4-yloxy]benzofuran-3-carboxamide, polymorph Form 6.
Figure 17:
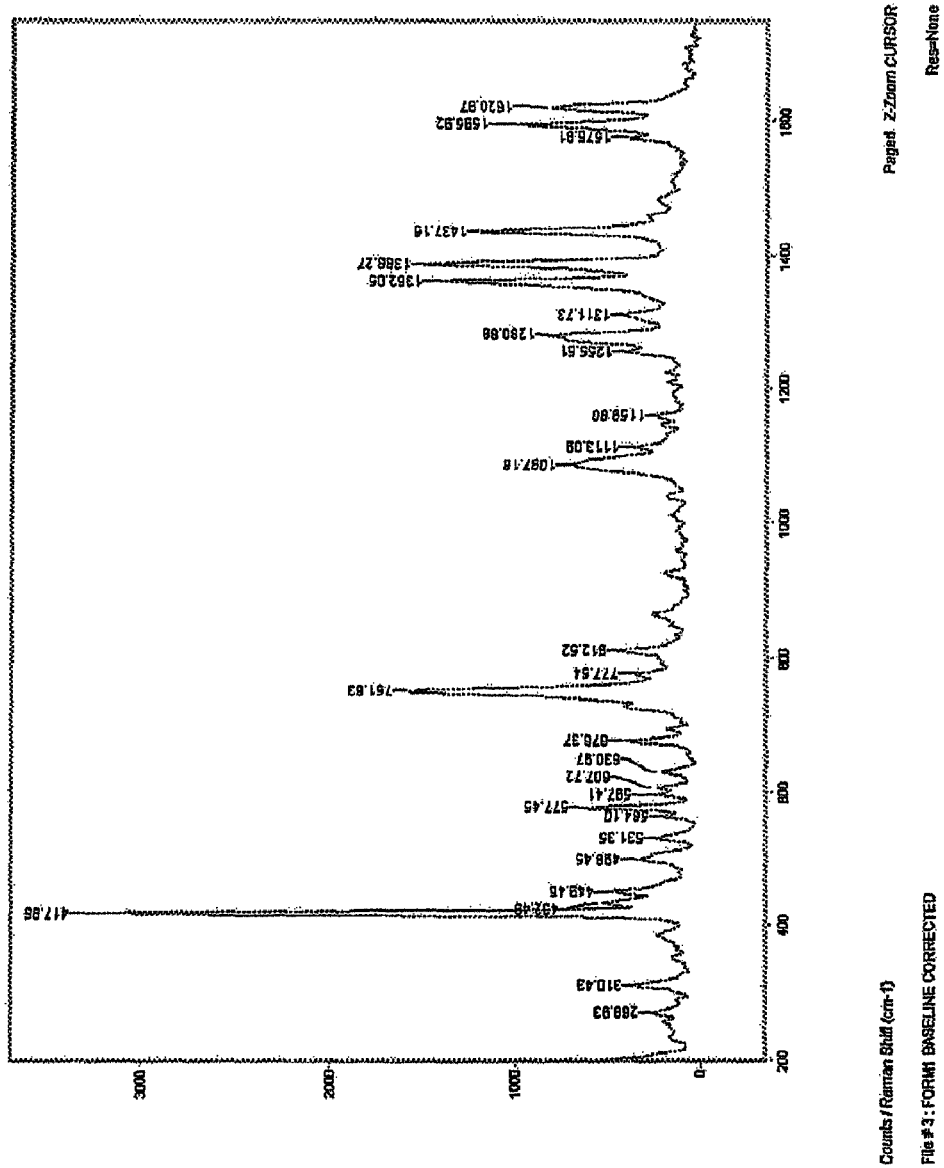
FIG. 17 shows a Raman spectrograph of free base N,2-dimethyl-6-[7-(2-morpholinoethoxy)quinolin-4-yloxy]benzofuran-3-carboxamide, polymorph Form 1.
Figure 18:
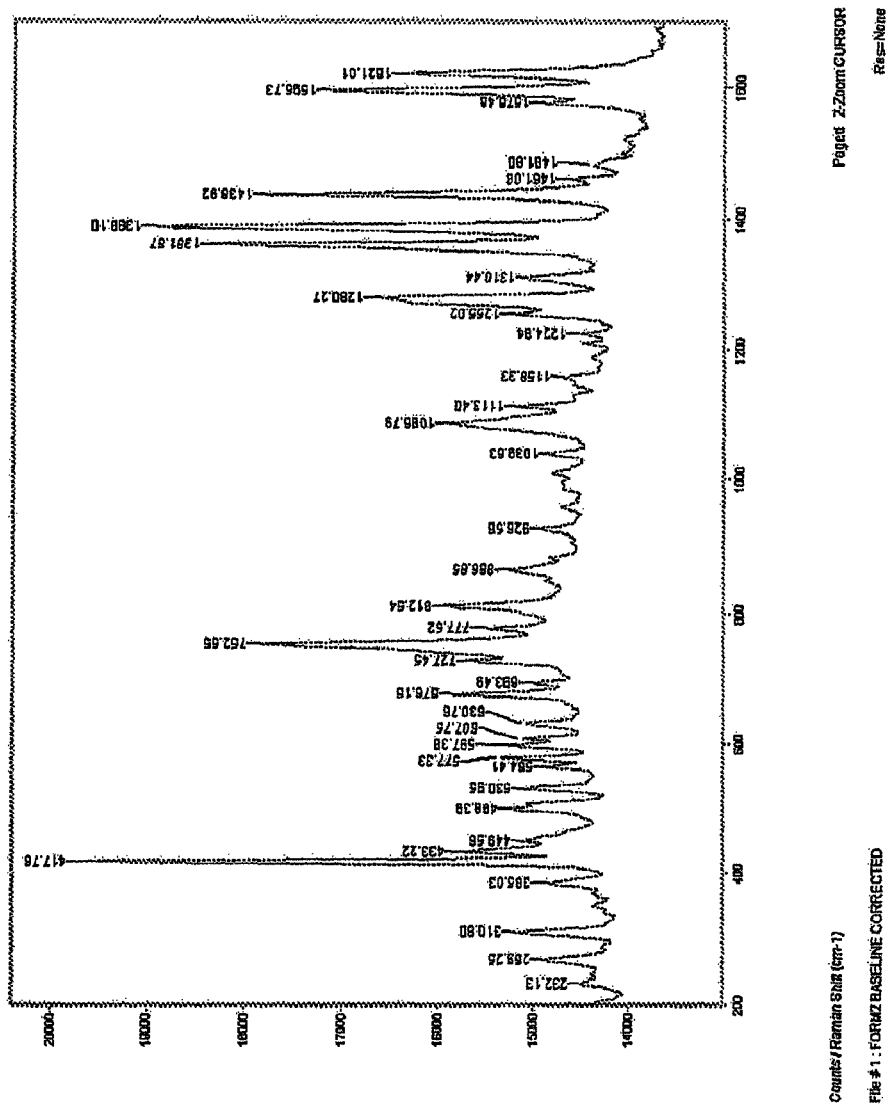
FIG. 18 shows a Raman spectrograph of free base N,2-dimethyl-6-[7-(2-morpholinoethoxy)quinolin-4-yloxy]benzofuran-3-carboxamide, polymorph Form 2.
Figure 19:
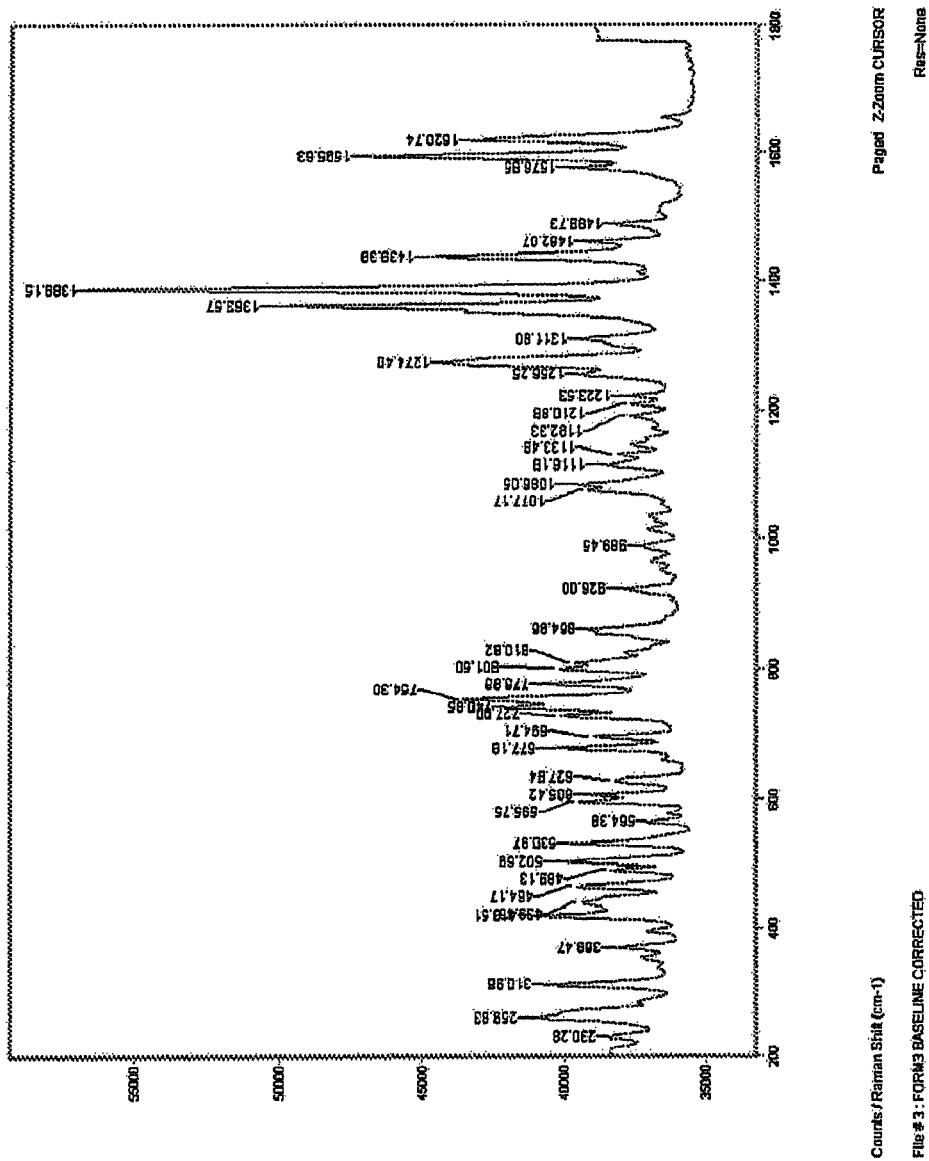
FIG. 19 shows a Raman spectrograph of free base N,2-dimethyl-6-[7-(2-morpholinoethoxy)quinolin-4-yloxy]benzofuran-3-carboxamide, polymorph Form 3.
Figure 20:
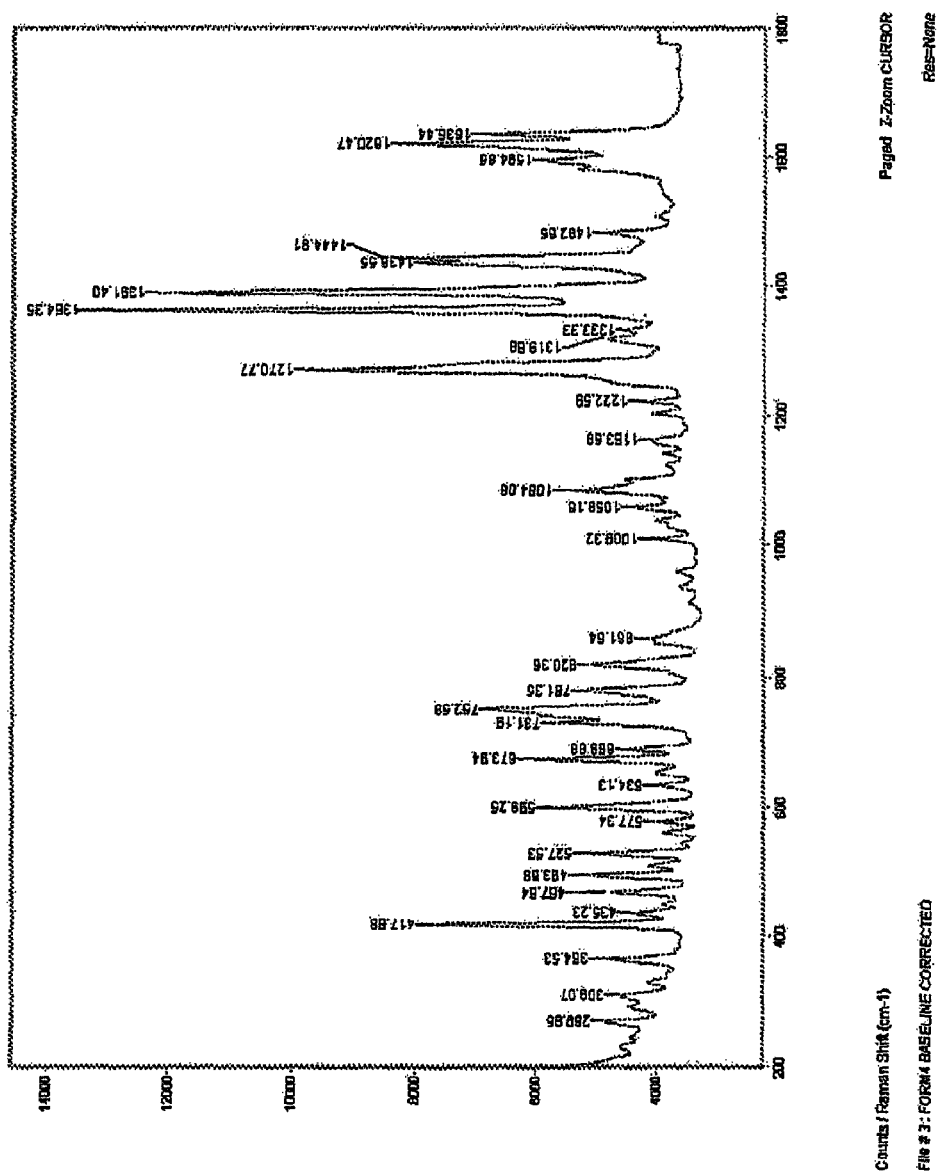
FIG. 20 shows a Raman spectrograph of free base N,2-dimethyl-6-[7-(2-morpholinoethoxy)quinolin-4-yloxy]benzofuran-3-carboxamide, polymorph Form 4.
Figure 21:
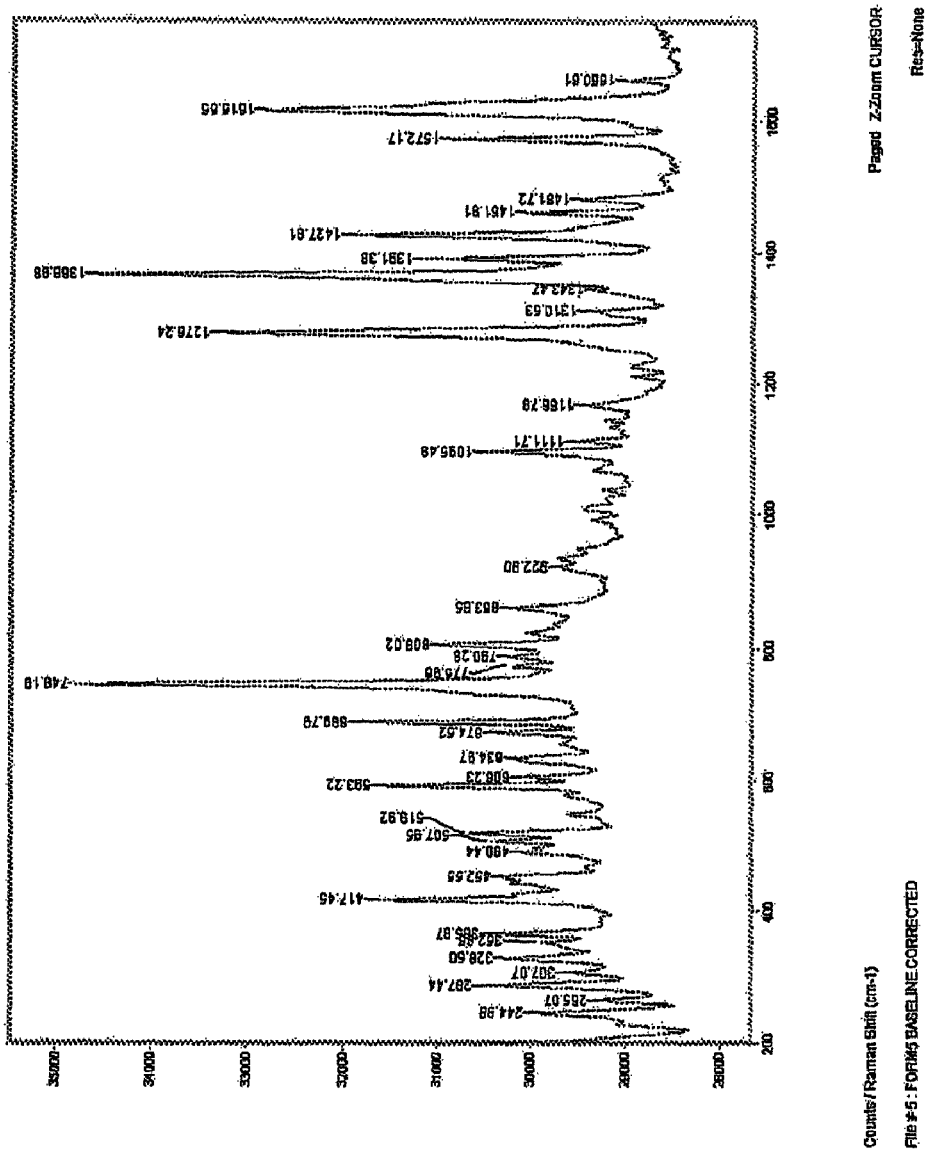
FIG. 21 shows a Raman spectrograph of free base N,2-dimethyl-6-[7-(2-morpholinoethoxy)quinolin-4-yloxy]benzofuran-3-carboxamide, polymorph Form 5.
Figure 22:
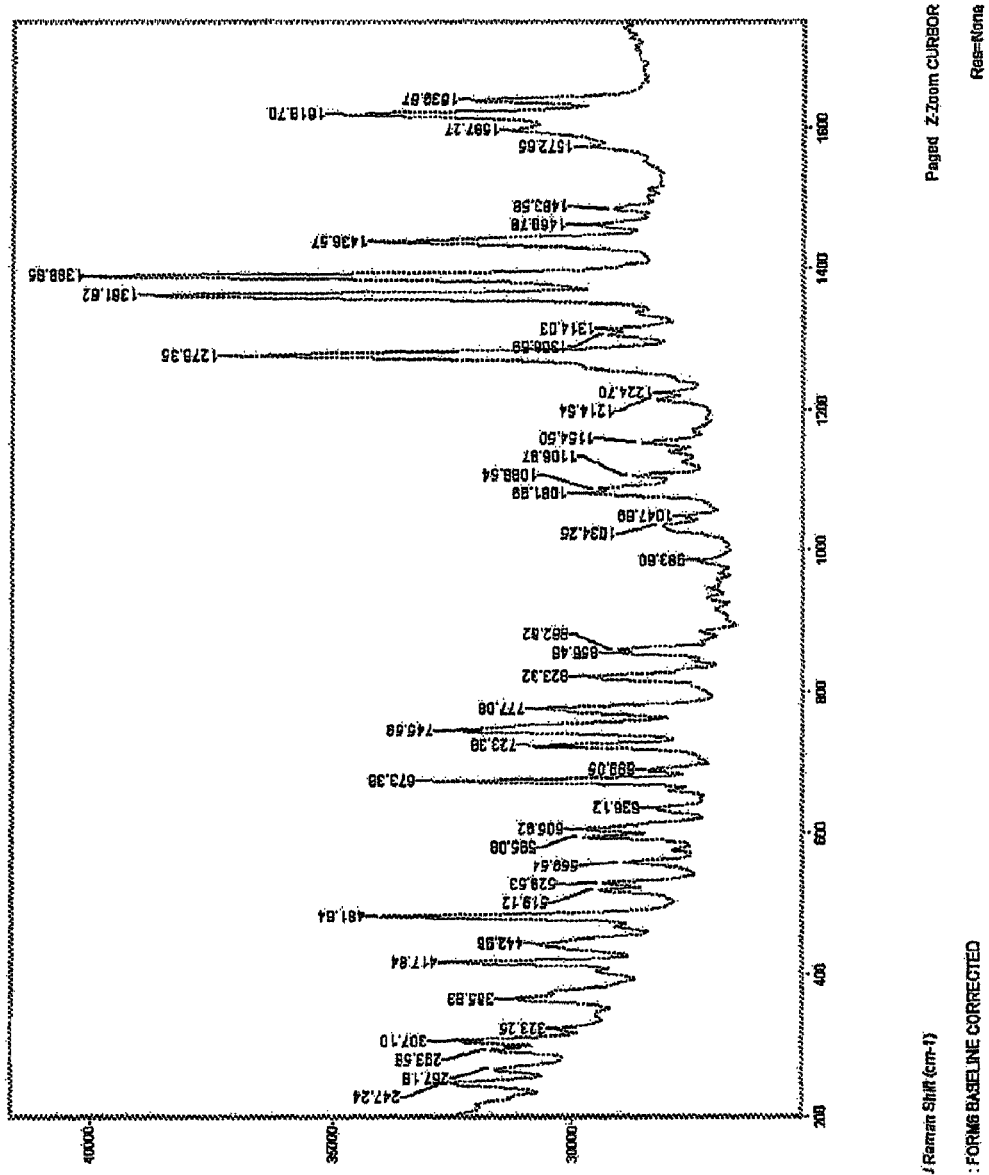
FIG. 22 shows a Raman spectrograph of free base N,2-dimethyl-6-[7-(2-morpholinoethoxy)quinolin-4-yloxy]benzofuran-3-carboxamide, polymorph Form 6.
Figure 23:
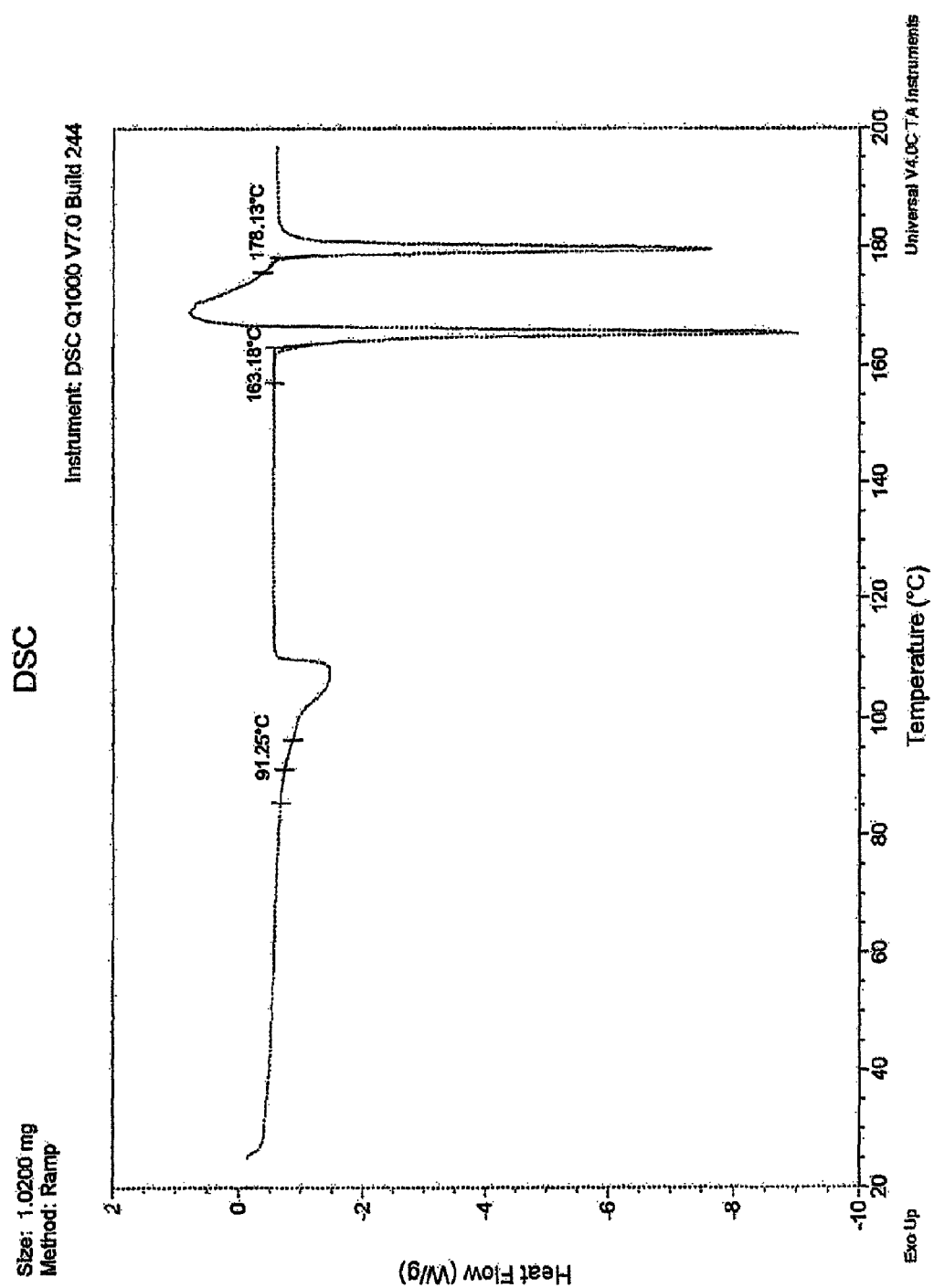
FIG. 23 shows a differential scanning calorimetery (DSC) thermogram of free base N,2-dimethyl-6-[7-(2-morpholinoethoxy)quinolin-4-yloxy]benzofuran-3-carboxamide, polymorph Form 1.
Figure 24:
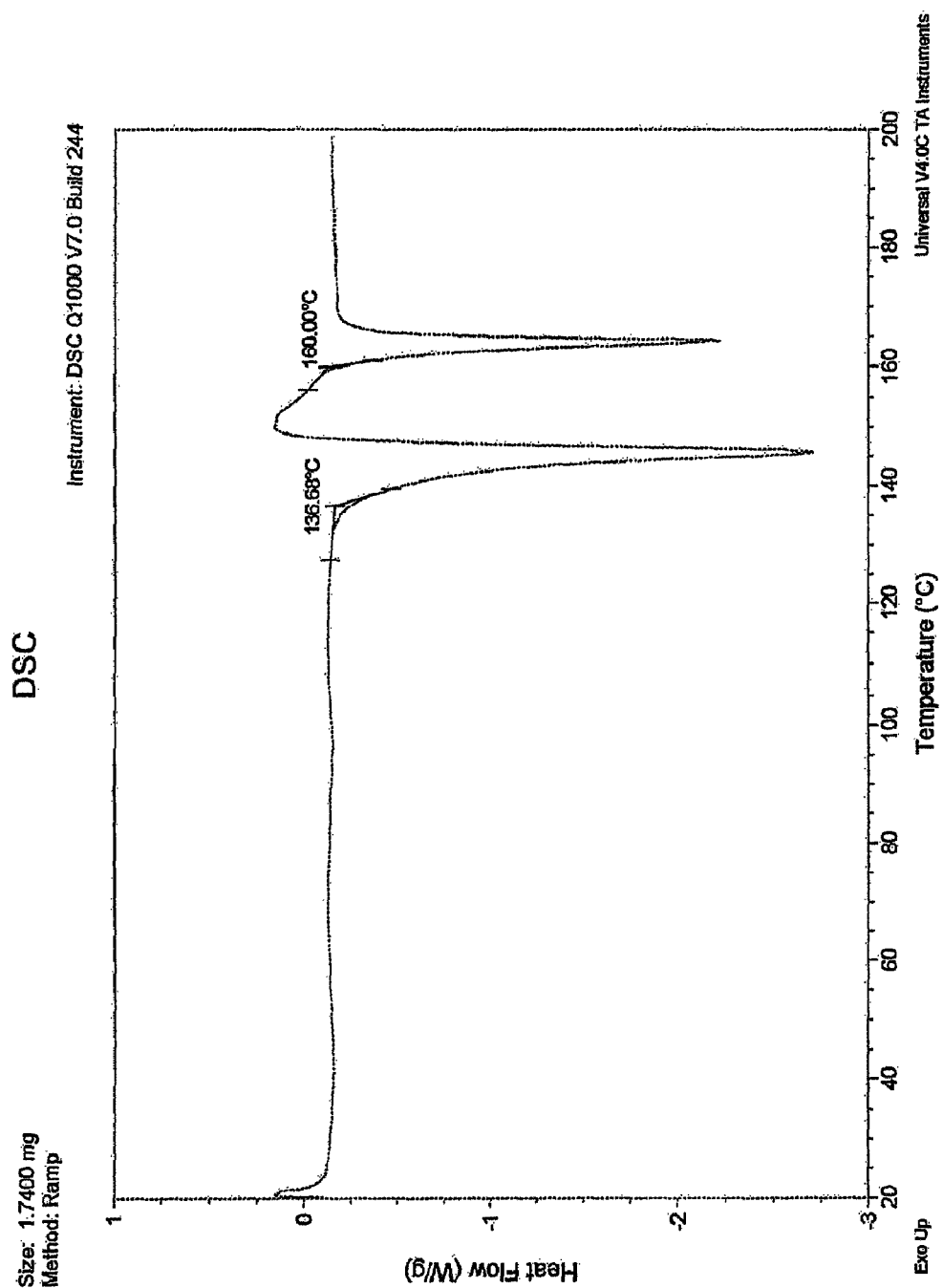
FIG. 24 shows a differential scanning calorimetery (DSC) thermogram of free base N,2-dimethyl-6-[7-(2-morpholinoethoxy)quinolin-4-yloxy]benzofuran-3-carboxamide, polymorph Form 2.
Figure 25:
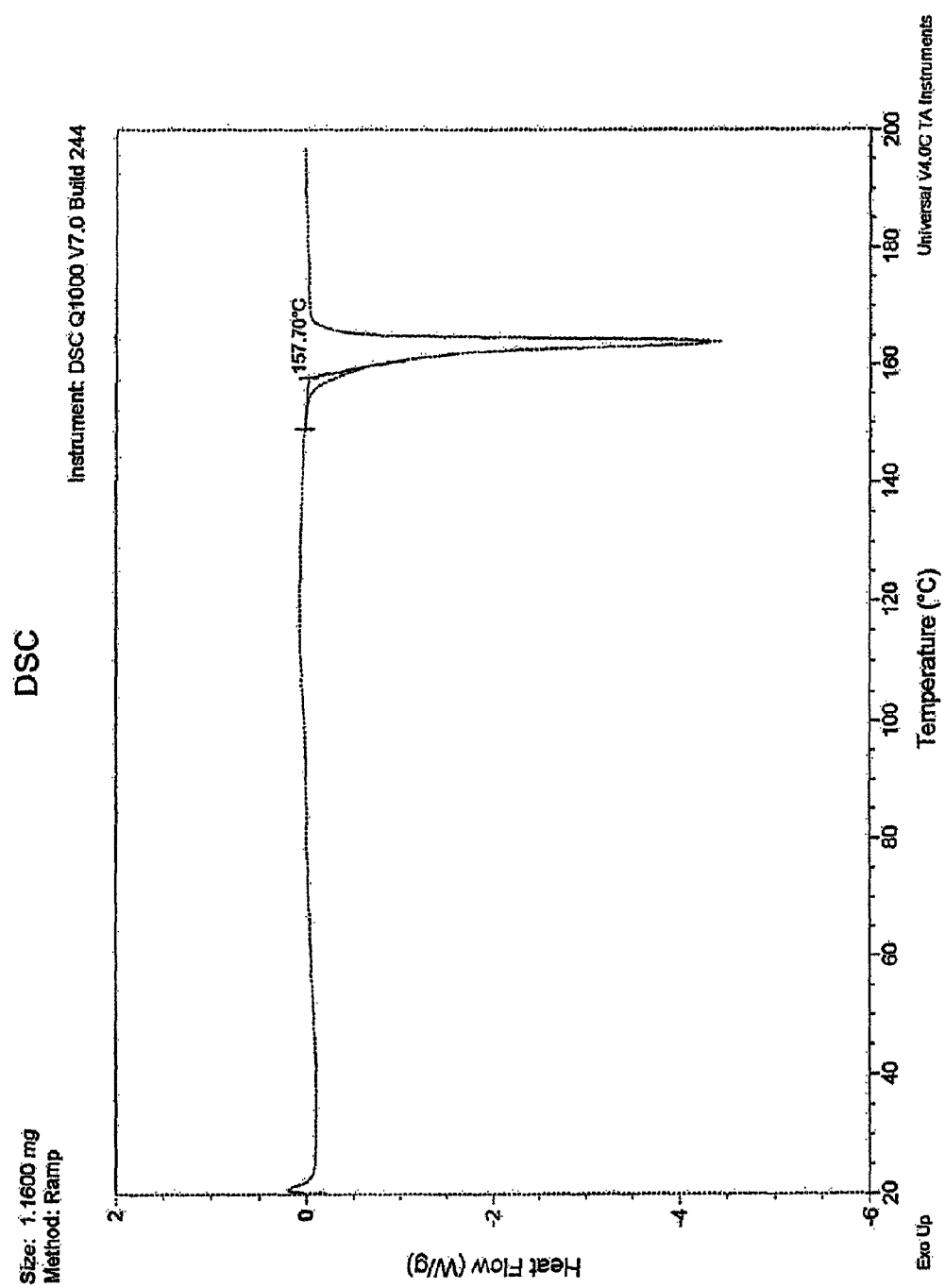
FIG. 25 shows a differential scanning calorimetery (DSC) thermogram of free base N,2-dimethyl-6-[7-(2-morpholinoethoxy)quinolin-4-yloxy]benzofuran-3-carboxamide, polymorph Form 3.
Figure 26:
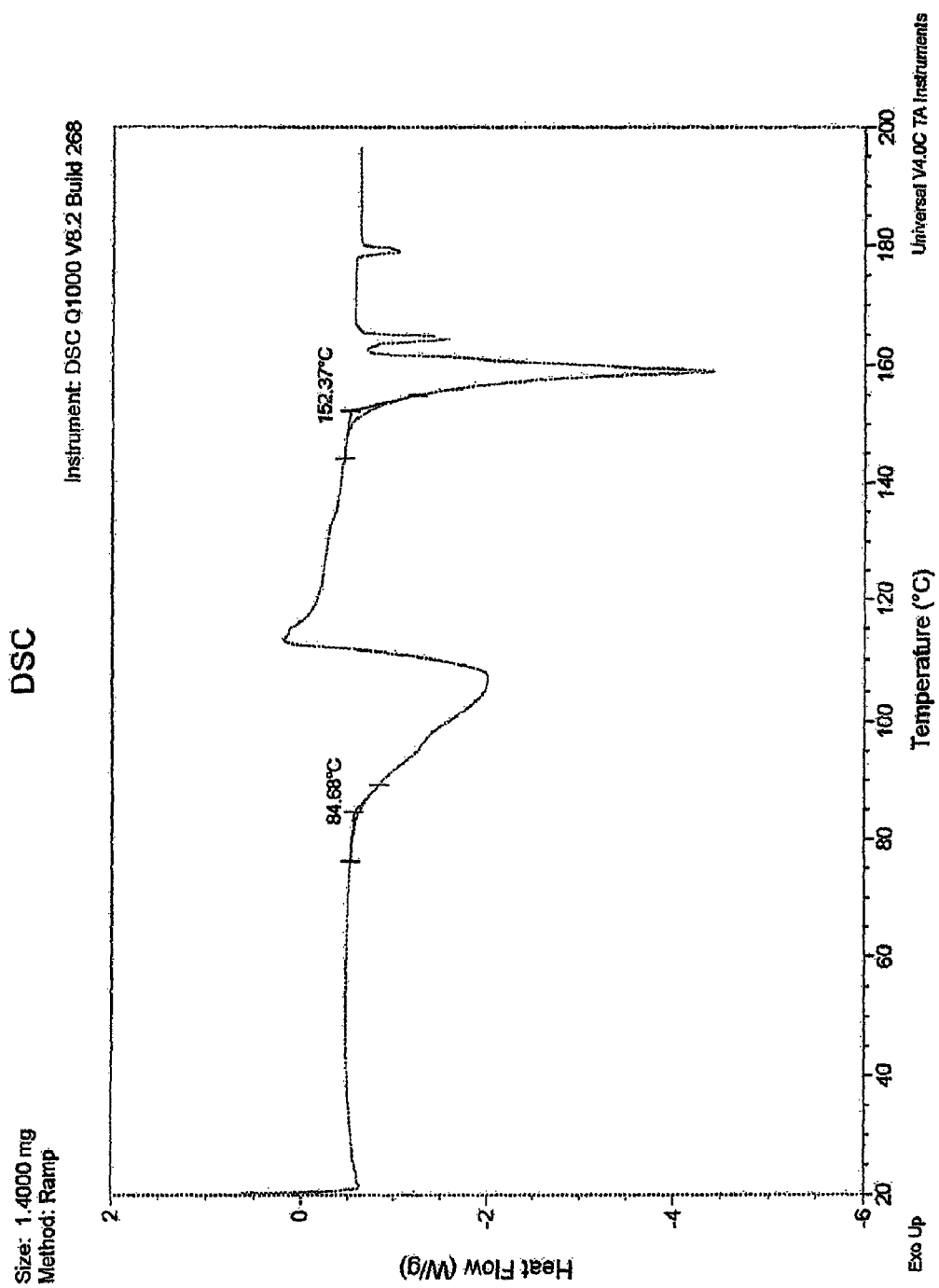
FIG. 26 shows a differential scanning calorimetery (DSC) thermogram of free base N,2-dimethyl-6-[7-(2-morpholinoethoxy)quinolin-4-yloxy]benzofuran-3-carboxamide, polymorph Form 4.
Figure 27:
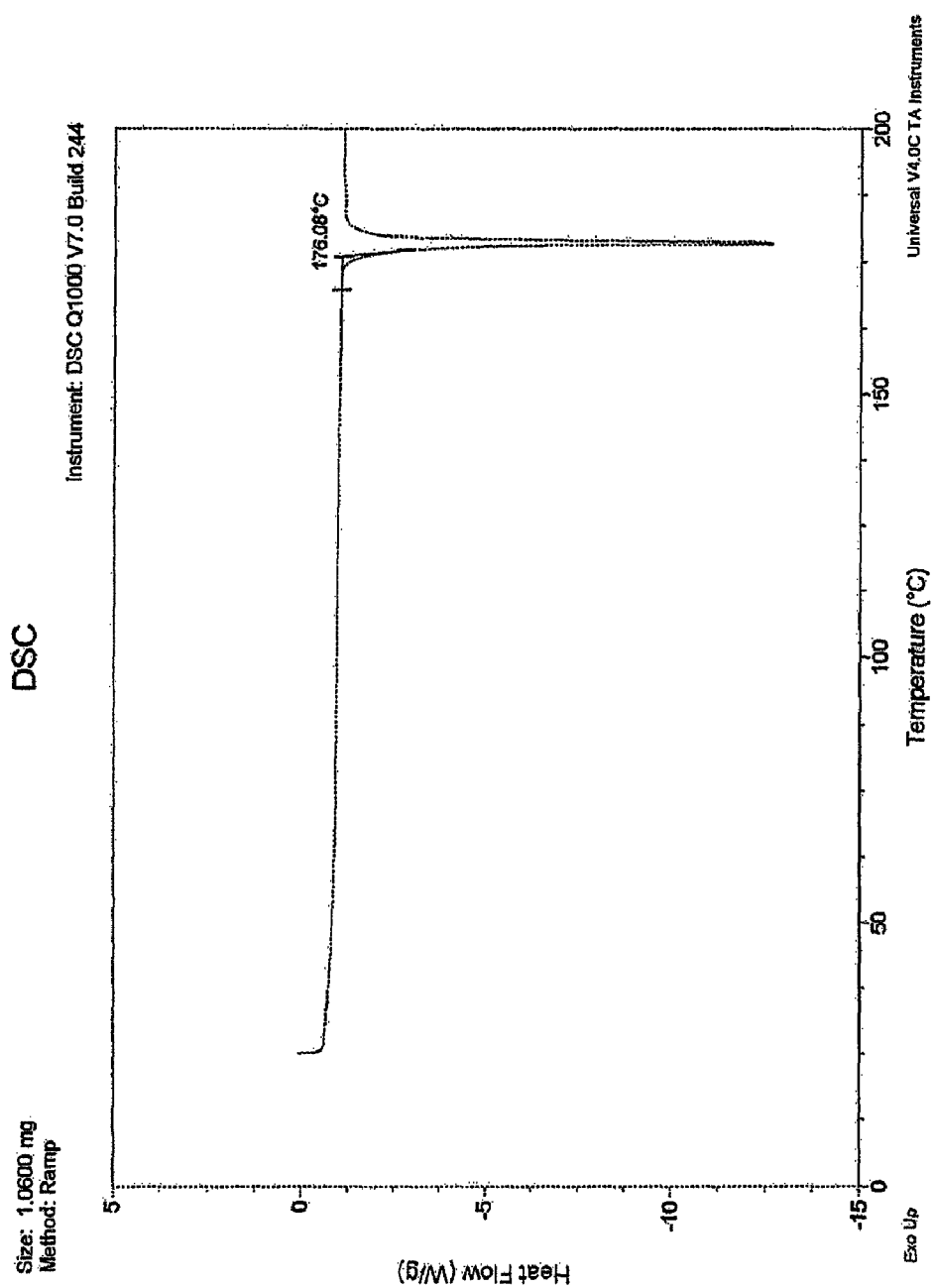
FIG. 27 shows a differential scanning calorimetery (DSC) thermogram of free base N,2-dimethyl-6-[7-(2-morpholinoethoxy)quinolin-4-yloxy]benzofuran-3-carboxamide, polymorph Form 5.
Figure 28:
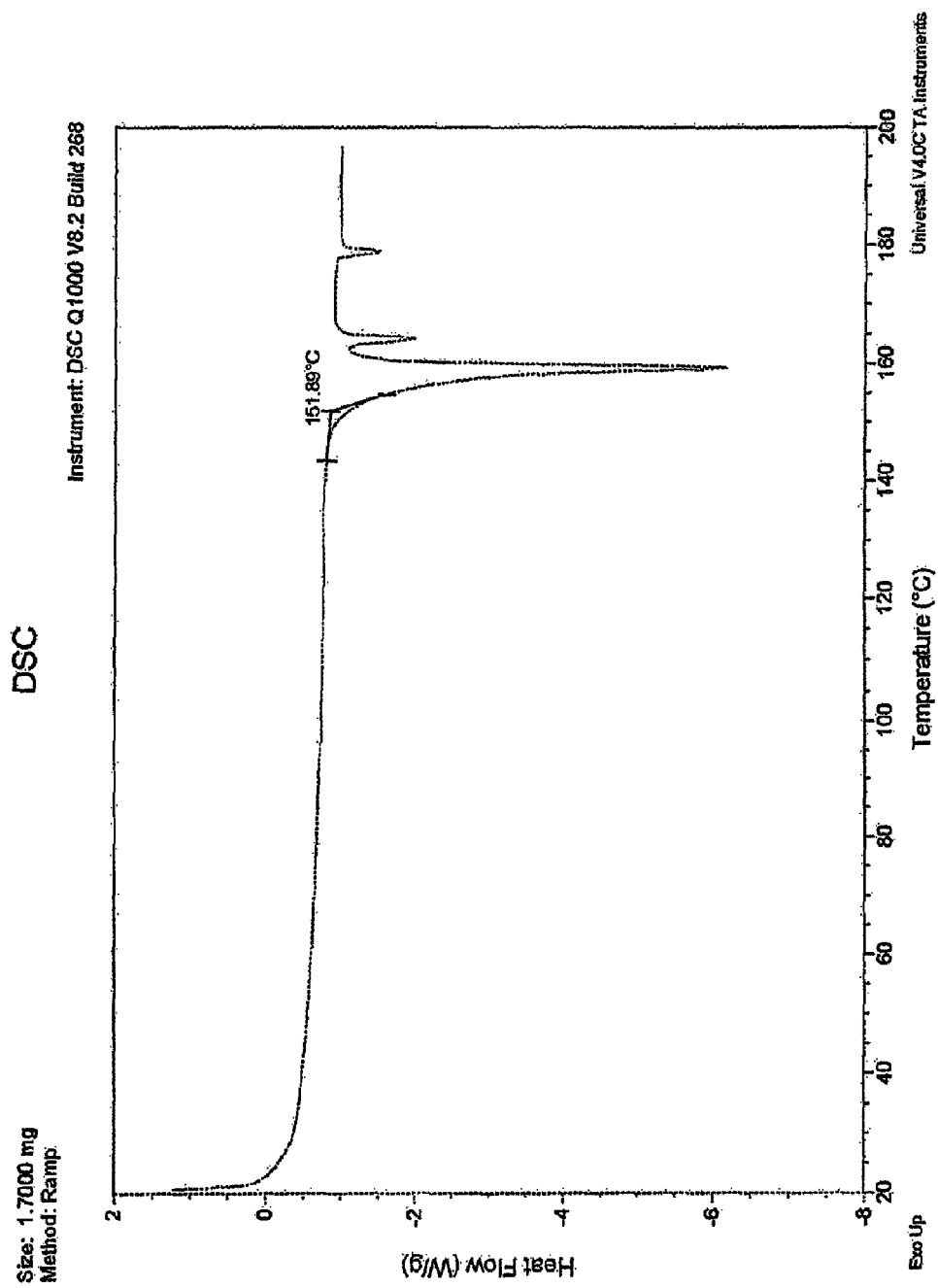
FIG. 28 shows a differential scanning calorimetery (DSC) thermogram of free base N,2-dimethyl-6-[7-(2-morpholinoethoxy)quinolin-4-yloxy]benzofuran-3-carboxamide, polymorph Form 6.

A solution of 4-(2-chloroethyl)morpholine (10.7 g, 57.4 mmol) and Cs$_2$CO$_3$ (46.3 g, 143.5 mmol) in DMF (100 mL) was stirred for 1 hour at room temperature. To the solution was added a solution of 6-[(7-hydroxyquinolin-4-yl)oxy]-N,2-dimethyl-1-benzofuran-3-carboxamide (10 g, 28.7 mmol). The mixture was heated to 120° C. for 15 hr. The solution was cooled to room temperature and extracted with EtOAc. The concentrated residue was purified by a silica gel column chromatography (using 5 to 10%) MeOH/CH$_2$Cl$_2$) to give 2.6 g of free base N,2-dimethyl-6-[7-(2-morpholinoethoxy)quinolin-4-yloxy]benzofuran-3-carboxamide as a solid. The solid free base was identified as Form 1 as characterized by powder X-ray diffraction as shown in FIG. 11. Note, Form 1 can also be prepared by slurrying any of Forms 3, 5, or 6 in water at room temperature for 24 hours.

Example 4

Preparation of Free Base Form 2

A solution of 4-(2-chloroethyl)morpholine (2.1 g, 11.5 mmol) and Cs$_2$CO$_3$ (7.5 g, 23 mmol) in CH$_3$CN (100 mL) was stirred for 45 minutes at room temperature. To the solution was added 6-[(7-hydroxyquinolin-4-yl)oxy]-N,2-dimethyl-1-benzofuran-3-carboxamide (2 g, 5.75 mmol). The mixture was heated to reflux for 3 hrs. Inorganic salt was removed by filtration and the solution was concentrated. The residue was purified by a silica gel column chromatography (using 1 to 10% MeOH/CH$_2$Cl$_2$) to give 1.8 g of free base N,2-dimethyl-6-[7-(2-morpholinoethoxy)quinolin-4-yloxy]benzofuran-3-carboxamide as a solid. The compound was then dissolved in hot isopropanol and stirred at room temperature overnight. 1.13 g of N,2-dimethyl-6-[7-(2-morpholinoethoxy)quinolin-4-yloxy]benzofuran-3-carboxamide as polymorph Form 2 was collected by filtration. Note, Form 2 is anhydrous and must be prepared under water-free conditions in order to prevent hydrate formation (such as Form 4 as described in Example 6).

Example 5

Preparation of Free Base Form 3

Form 3 was prepared by heating Form 1 (0.1 g) at 110° C. in an oven for 1 hour under vacuum.

Example 6

Preparation of Free Base Form 4

Form 4 was prepared by treating Form 1 (0.1 g) with 3.0 mL isopropyl alcohol and heating to 70° C. to obtain a solution. Following the complete dissolution, the solution was cooled to ambient temperature. The precipitation filtered from the solution was identified as Form 4.

Example 7

Preparation Of Free Base Form 5

Form 5 was prepared by treating Form 1 (1 g) with 5.0 mL acetonitrile to form a suspension. The suspension was then stirred at 80° C. for 1 hr. to obtain conversion of Form 1 to Form 5.

Example 8

Preparation of Free Base Form 6

Form 6 was obtained by heating Form 4 (0.1 g) at 110° C. in an oven for 1 hr. under vacuum.

Example 9

Preparation of bis-Hbr Form I bis-HBr Form I was prepared as follows. A 20 mL scintillation vial was charged with 0.1 g of N,2-dimethyl-6-[7-(2-morpholinoethoxy)quinolin-4-yloxy]benzofuran-3-carboxamide and 10 mL of acetonitrile. The vial was stirred and heated to 72° C. and the temperature held for 5 minutes. A solution of HBr (0.152 mL, 3M in acetonitrile, 2.1 equiv.) was added sub-surface. The solution turned cloudy upon addition of the acid, but became clear after a few seconds. The temperature was held constant for 5 minutes. The solution was then cooled to room temperature at a rate of 20° C./hour. The vial was then placed in a cold bath (or refrigerator at 2° C.) for 2 hours. The solid was collected by vacuum filtration and dried in vacuo (30 inch Hg, 60° C.) overnight. The solid was then slurried in acetone (25 mg/mL) at room temperature for 2 hrs, and then dried in vacuo oven at 60° C. overnight.

Example 10

Preparation of bis-Hbr Form II

Bis-HBr Form II was prepared from bis-HBr-Form I by placing Form I in an open container at 40° C. and 75% RH for 4 weeks.

Example 11

Preparation of Amorphous bis-maleate

Approximately 4 mg of N,2-dimethyl-6-[7-(2-morpholinoethoxy)quinolin-4-yloxy]benzofuran-3-carboxamide-bis-maleate salt was dissolved in 1 mL methanol. The solution was placed and dried in a vacuum oven at 40° C. for 30 minutes to obtain the amorphous form.

Example 12

Preparation of Amorphous Free Base

Approximately 4 mg of free base N,2-dimethyl-6-[7-(2-morpholinoethoxy)quinolin-4-yloxy]benzofuran-3-carboxamide was dissolved in 2 mL methanol:ethanol mixture (50:50). The solution was placed and dried in a vacuum oven at 40° C. for 30 minutes to obtain the amorphous form.

We claim:

1. A bis-maleate salt of N,2-dimethyl-6-[7-(2-morpholinoethoxy)quinolin-4-yloxy]benzofuran-3-carboxamide, wherein said salt is a crystalline anhydrous salt and has a powder X-ray diffraction pattern comprising peaks at diffraction angles (2θ) of 4.0±0.1, 8.1±0.1, 18.1±0.1, 18.6±0.1, 21.6±0.1, and 26.2±0.1.

2. A bis-maleate salt of N,2-dimethyl-6-[7-(2-morpholinoethoxy)quinolin-4-yloxy]benzofuran-3-carboxamide, wherein said salt is a crystalline anhydrous salt and has a solid state NMR spectrum comprising $^{13}C$ chemical shifts at 118.0±0.1, 124.2±0.1, 143.9±0.1, 148.0±0.1, and 162.5±0.1 ppm.

3. A bis-maleate salt of N,2-dimethyl-6-[7-(2-morpholinoethoxy)quinolin-4-yloxy]benzofuran-3-carboxamide, wherein said salt is a crystalline hydrate salt and has a powder X-ray diffraction pattern comprising peaks at diffraction angles (2θ) of 6.4±0.1, 12.7±0.1, and 17.3±0.1.

4. A bis-maleate salt of N,2-dimethyl-6-[7-(2-morpholinoethoxy)quinolin-4-yloxy]benzofuran-3-carboxamide, wherein said salt is a crystalline hydrate salt and has a solid state NMR spectrum comprising $^{13}C$ chemical shifts at 99.2±0.1, 125.8±0.1, 132.8±0.1, 142.2±0.1, and 166.1±0.1 ppm.

* * * * *